United States Patent
Konradi et al.

(10) Patent No.: US 6,545,160 B2
(45) Date of Patent: Apr. 8, 2003

(54) αAMINOCETIC ACID DERIVATIVES- $\alpha_4\beta_7$ RECEPTOR ANTAGONISTS

(75) Inventors: Andrei W. Konradi, San Francisco, CA (US); Michael A. Pleiss, Sunnyvale, CA (US); Eugene D. Thorsett, Half Moon Bay, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/147,884

(22) Filed: May 20, 2002

(65) Prior Publication Data

US 2003/0018195 A1 Jan. 23, 2003

Related U.S. Application Data

(62) Division of application No. 09/514,773, filed on Feb. 28, 2000, now Pat. No. 6,410,781.
(60) Provisional application No. 60/122,071, filed on Mar. 1, 1999.

(51) Int. Cl.[7] .................... C07D 263/06; A61K 31/445
(52) U.S. Cl. .................... 548/230; 544/59; 546/333; 548/228; 548/229; 560/132; 560/133; 514/227.5; 514/478; 514/357; 514/376; 514/548
(58) Field of Search .................... 560/133, 132; 548/229, 230; 544/59; 546/333; 514/227.5, 357, 478, 548, 376

(56) References Cited

U.S. PATENT DOCUMENTS

| | | | |
|---|---|---|---|
| 4,085,057 A | 4/1978 | Masuda et al. | |
| 4,438,122 A | 3/1984 | Holmwood et al. | |
| 4,505,910 A | 3/1985 | Bagli | |
| 4,518,600 A | 5/1985 | Holmwood et al. | |
| 4,544,402 A | 10/1985 | Schnurbusch et al. | |
| 4,559,345 A | 12/1985 | Gomarasca et al. | |
| 4,672,065 A | 6/1987 | Spatz | |
| 4,908,368 A | 3/1990 | Murase et al. | |
| 4,959,364 A | 9/1990 | Mueller et al. | |
| 4,992,439 A | 2/1991 | Meanwell | |
| 5,030,644 A | 7/1991 | Baldwin et al. | |
| 5,120,734 A | 6/1992 | Klausener et al. | |
| 5,238,934 A | 8/1993 | Knuppel et al. | |
| 5,278,184 A | 1/1994 | Artico et al. | |
| 5,510,331 A | 4/1996 | Kogan et al. | |
| 5,580,868 A | 12/1996 | Lunkenheimer et al. | |
| 5,728,686 A | 3/1998 | Billen et al. | |
| 5,770,573 A | 6/1998 | Arrhenius et al. | |
| 5,814,643 A | 9/1998 | Duggan et al. | |
| 5,861,429 A | 1/1999 | Sato et al. | |
| 5,925,644 A | 7/1999 | Jakobi et al. | |
| 5,942,504 A | 8/1999 | Grobelny | |
| 5,955,491 A | 9/1999 | Sohda et al. | |
| 5,962,479 A | 10/1999 | Chen | |
| 5,972,946 A | 10/1999 | Murata et al. | |
| 6,005,117 A | 12/1999 | Wehner et al. | |
| 6,410,781 B1 * | 6/2002 | Konradi et al. | 560/133 |

FOREIGN PATENT DOCUMENTS

| | | |
|---|---|---|
| DE | 19713000 | 10/1998 |
| EP | 0 288 176 | 10/1988 |
| EP | 0 330 506 | 8/1989 |
| EP | 0 042 945 A2 | 5/1998 |
| EP | 0 842 943 A1 | 5/1998 |
| GB | 1201121 * | 8/1970 |
| WO | 96/01644 | 1/1996 |
| WO | 97/23451 | 7/1997 |
| WO | 98/00395 | 1/1998 |
| WO | 99/06390 | 2/1999 |
| WO | 99/06391 | 2/1999 |
| WO | 99/10312 | 3/1999 |
| WO | 99/10313 | 3/1999 |
| WO | 99/37605 | 7/1999 |
| WO | 99/37618 | 7/1999 |
| WO | 99/52898 | 10/1999 |

OTHER PUBLICATIONS

Norman et al, Tetrahedron Lett., vol. 33, No. 45, pp 6803–6806, 1992.*
Hladon, B., et al., "In Vitro cytostatic activity of some amino acid 4–N–substituted cytosines" Arch. Immunol. Ther. Exp. 40(2):145–50 (1992).
Hoffman, et al. "N–Pyrimidinylamino acids. III. N–(oxopyrimidinyl) derivatives of neutral amino acids" Z. Chem. 12(1): 21–2, Coden: Zeceal (1972).
Teranishi, et al. "Synthesis and Chemiluminescense of Coelenterazine (Oplophorus Luciferin) analogs" Bull. Chem. Soc. Jpn. 63(11): 3132–40 (1990) (Abstract).
Abraham, et al., J. Clin. Invest. 93:776 (1994).
Bao, et al. Diff. 52:239 (1993).
Baron, et al. J. Exp. Med. 177:57 (1993).
Baron, et al. J. Clin. Invest. 93:1700 (1994).
Burkly, et al. Diabetes. 43:529 (1994).
Cybulsky, et al. Science. 251:788 (1991).
Elices, et al. J. Clin. Invest. 93:405 (1994).
Elices, et al. Cell. 60:577–584 (1990).
Hamann, et al. J. Immunology. 152:3283 (1994).
Kawaguchi, et al. Japanese J. Cancer Res. 83:1304 (1992).
Lauri, et al. British J. Cancer. 68:862 (1993).
Li, et al. Arterioscler. Thromb. 13:197 (1993).
Mulligan, et al. J. Immunology. 150:2407 (1993).

(List continued on next page.)

Primary Examiner—Shailendra Kumar
(74) Attorney, Agent, or Firm—Burns, Doane, Swecker & Mathis LLP

(57) ABSTRACT

Disclosed are compounds which bind $\alpha_4\beta_7$ integrin. Certain of these compounds also inhibit leukocyte adhesion and, in particular, leukocyte adhesion mediated by $\alpha_4\beta_7$ integrin. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

34 Claims, No Drawings

OTHER PUBLICATIONS

Okarhara, et al. *Can. Res.*, 54:3233 (1994).
Osborn. *Cell.* 62:3–6 (1990).
Paavonen, et al. *Int. J. Can.* 58:298 (1994).
Paul, et al. *Transpl. Proceed.* 25:813 (1993).
Postigo, et al. *J. Clin. Invest.* 89:1445 (1991).
Pretolani, et al. *J. Exp. Med.* 180:795 (1994).
Sasseville, et al. *Am. J. Path.* 144:27 (1994).
Schadendorf, et al. *J. Path.* 170:429 (1993).
Springer. *Nature.* 346:425–434 (1990).
Tidswell, et al. *J of Immunolgy.* 1497–1505 (1997).
van Dinther–Janssen, et al. *Annals. Rheumatic Dis.* 52:672 (1993).
van Dinther–Janssen, et al. *J. Immunology.* 147:4207 (1991).
Vedder, et al. *Surgery.* 106:509 (1989).
Yang, et al. *Proc. Nat. Acad. Science (USA).* 90:10494 (1993).
Yednock, et al. *Nature.* 356:63 (1992).

* cited by examiner

αAMINOCETIC ACID DERIVATIVES- $\alpha_4\beta_7$ RECEPTOR ANTAGONISTS

RELATED APPLICATION

This application is a divisional of application Ser. No. 09/514,773, filed on Feb. 28, 2000, now U.S. Pat. No. 6,410,781 which issued on Jun. 25, 2002.

This application claims priority under 35 U.S.C. §119(e) to U.S. Provisional application Serial No. 60/122,071, filed on Mar. 1, 1999, the disclosure of which is incorporated herein in its entirety.

BACKGROUND OF THE INVENTION

1. Field of the Invention

This invention relates to compounds which inhibit leukocyte adhesion and, in particular, leukocyte adhesion mediated by $\alpha_4\beta_7$. Accordingly, compounds of this invention are useful in the treatment and prevention of diseases mediated by $\alpha_4\beta_7$ binding and cell adhesion and activation such as multiple sclerosis, asthma, allergic rhinitis, rheumatoid arthritis, septic arthritis, restenosis, inflammatory bowel disease including ulcerative colitis and Crohn's disease, dernatitis, psoriasis, and the like.

2. State of the Art

REFERENCES

The following publications, patents and patent applications are cited in this application as superscript numbers:

1. Tidswell, et al., *J. of Immunology.*, 1497–1505 (1997)
2. Springer, *Nature*, 3:425–434 (1990)
3. Osborn, *Cell*, 62:3–6 (1990)
4. Vedder, et al., *Surgery*, 106:509 (1989)
5. Pretolani, et al., *J. Exp. Med.*, 180:795 (1994)
6. Abraham, et al., *J. Clin. Invest.*, 93:776 (1994)
7. Mulligan, et al., *J. Immunology*, 150:2407 (1993)
8. Cybulsky, et al., *Science*, 251:788 (1991)
9. Li, et al., *Arterioscler. Thromb.*, 11:197 (1993)
10. Sasseville, et al., *Am. J. Path.*, 144:27 (1994)
11. Yang, et al., *Proc. Nat. Acad. Science (USA)*, 90:10494 (1993)
12. Burkly, et al., *Diabetes*, 43:529 (1994)
13. Baron, et al., *J. Clin. Invest.*, 93:1700 (1994)
14. Hamnann, et al., *J. Immunology*, 152:3238 (1994)
15. Yednock, et al., *Nature*, 356:63 (1992)
16. Baron, et al., *J. Exp. Med.*, 177:57 (1993)
17. van Dinther-Janssen, et al., *J. Immunology*, 147:4207 (1991)
18. van Dinther-Janssen, et al., *Annals. Rheumatic Dis.*, 5:672 (1993)
19. Elices, et al., *J. Clin. Invest.*, 23:405 (1994)
20. Postigo, et al., *J. Clin. Invest.*, 89:1445 (1991)
21. Paul, et al., *Transpl. Proceed.*, 25:813 (1993)
22. Okarhara, et al., *Can. Res.*, 54:3233 (1994)
23. Paavonen, et al., *Int. J. Can.*, 58:298 (1994)
24. Schadendorf, et al., *J. Path.*, 170:429 (1993)
25. Bao, et al., *Diff.*, 52:239 (1993)
26. Lauri, et al., *British J. Cancer*, 68:862 (1993)
27. Kawaguchi, et al., *Japanese J. Cancer Res.*, 8:1304 (1992)
28. Kogan, et al., U.S. Pat. No. 5,510,332, issued Apr. 23, 1996
29. International Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

Integrins are heterodimeric adhesion receptors that mediate cell-cell and cell-extracellular matrix interactions. The $\beta_7$ integrin subfamily has two known members: $\alpha_4\beta_7$ and $\alpha_E\beta_7$. These $\beta_7$ integrins are expressed primarily by leukocytes. $\beta_7$ integrins are unique among known integrins in their ability to recognize certain ligands expressed on the surface of endothelial and epithelial cells in mucosal organs.

$\alpha_4\beta_7$ is a lymphocyte homing receptor and plays a crucial role in the migration of these cells to the intestine and associated lymphoid tissue, such as Peyer's patches in the intestine. $\alpha_4\beta_7$ mediates adhesion to a ligand on Peyer's patch high endothelial venules ("HEV[4]"). The ligand on Peyer's patch HEV is MAdCAM-1, a glycoprotein in the Ig superfamily. MAdCAM-1 is expressed on Peyer's patch HEV, mesenteric lymph node HEV, and lamnina propria venules within the gut. Antibodies against $\alpha_4$ or $\beta_7$ subunits inhibit attachment of circulating lymphocytes to Peyer's patch HEV in vivo.[1]

Memory T cells that circulate preferentially to intestinal tissues express high levels of $\alpha_4\beta_7$, whereas those that circulate to other organs are mostly $\alpha_4\beta_7$. These $\alpha_4\beta_7$ memory T cells express a related integrin, $\alpha_4\beta_1$, which is not able to mediate cell adhesion to MAdCAM-1. However, both $\alpha_4\beta_7$ and $\alpha_4\beta_1$ can mediate adhesion to VCAM-1 and to fibronectin.

Intercellular adhesion mediated by $\alpha_4\beta_7$ and other cell surface receptors is associated with a number of inflammatory responses. At the site of an injury or other inflammatory stimulus, activated vascular endothelial cells express molecules that are adhesive for leukocyes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[2] and Osborn[3].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[4]). Other inflammatory conditions mediated by an adhesion mechanism include, by way of example, asthma[5-7], Alzheimer's disease, atherosclerosis[8-9], AIDS dementia[10], diabetes[11-13] (including acute juvenile onset diabetes), inflammatory bowel disease[14] (including ulcerative colitis and Crohn's disease), multiple sclerosis[15-16], rheumatoid arthritis[17-20], tissue transplantation[21], tumor metastasis[22-27], meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

In view of the above, assays for determining the $\alpha_4\beta_7$ level in a biological sample containing $\alpha_4\beta_7$ would be useful, for example, to diagnosis $\alpha_4\beta_7$ mediated conditions. Additionally, despite these advances in the understanding of leukocyte adhesion, the art has only recently addressed the use of inhibitors of adhesion in the treatment of inflammatory brain diseases and other inflammatory conditions[28,29]. The present invention addresses these and other needs.

SUMMARY OF THE INVENTION

In one aspect, this invention provides compounds of Formula I:

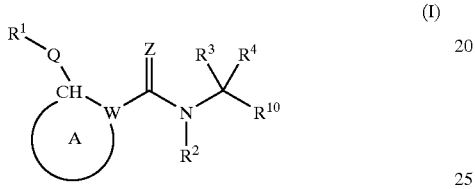

wherein:
A together with —CH— and W forms a cyclic group selected from the group consisting of heterocyclic, substituted heterocyclic, cycloalkyl, and substituted cycloalkyl;

Q is selected from the group consisting of alkylene, substituted alkylene, —CO—, —NR$^5$— (where R$^5$ is hydrogen, alkyl, or acyl), —O—, or —S(O)$_q$ where q is an integer from 0 to 2;

W is —CH— or —N—;

Z is —O— or —S—;

R$^1$ is selected from the group consisting of aryl, substituted aryl, heteroaryl, substituted heteroaryl, heterocyclic, substituted heterocyclic, cycloalkyl, and substituted cycloalkyl;

R$^2$ is selected from the group consisting of hydrogen, alkyl which is optionally substituted with one to four substituents independently selected from R$^a$ and Cy which is optionally substituted with one to four substituents independently selected from R$^b$ wherein R$^a$ and R$^b$ are as defined below;

R$^3$ is selected from the group consisting of:
(a) -(alkylene)-Ar—R$^6$, -(alkenylene)-Ar—R$^6$, or -(alkynylene)-Ar—R$^6$ where:
Ar is selected from the group consisting of aryl, heteroaryl, or heterocyclic wherein said aryl, heteroaryl, and heterocyclic rings are optionally substituted with one or two substituents independently selected from R$^a$ wherein R$^a$ is as defined below;
R$^6$ is selected from the group consisting of —O—Y—NR$^7$R$^8$ and —O—Y—R$^9$ wherein Y is selected from the group consisting of —C(O)— and —SO$_2$—; R$^7$ and R$^8$ are independently selected from the group consisting of hydrogen, alkyl, substituted alkyl, cycloalkyl, heterocyclic, and substituted heterocyclic; or R$^7$ and R$^8$ are joined to form a heterocycle or substituted heterocycle; and R$^9$ is heterocycle or substituted heterocycle;

(b) -(alkyene)-Ar$^2$—Ar$^1$, -(alkenylene)-Ar$^2$—Ar$^1$ and -(alkynylene)-Ar$^2$—Ar$^1$, wherein Ar$^1$ and Ar$^2$ are independently aryl or heteroaryl each of which is optionally substituted with one to four substituents independently selected from R$^b$ as defined below; and alkylene, alkenylene and alkynylene are optionally substituted with one to four substituents independently selected from R$^a$ as defined below;

R$^4$ is selected from the group consisting of hydrogen, alkyl, alkenyl, alkynyl, aryl, aryl-C$_{1-10}$alkyl, heteroaryl, and heteroaryl-C$_{1-10}$ alkyl wherein alkyl, alkenyl and alkynyl are optionally substituted with one to four substituents selected from R$^a$ as defined below; and aryl and heteroaryl are optionally substituted with one to four substituents independently selected from R$^b$ as defined below;

R$^a$ is selected from the group consisting of Cy, —OR$^d$, —NO$_2$, halogen —S(O)$_m$R$^d$, —SR$^d$, —S(O)$_2$OR$^d$, —S(O)$_m$NR$^d$R$^e$, —NR$^d$R$^e$, —O(CR$^f$R$^g$)$_n$NR$^d$R$^e$, —C(O)R$^d$, —CO$_2$R$^d$, —CO$_2$(CR$^f$R$^g$)$_n$CONR$^d$R$^e$, —OC(O)R$^d$, —CN, —C(O)NR$^d$R$^e$, —NR$^d$C(O)R$^e$, —OC(O)NR$^d$R$^e$, —NR$^d$C(O)OR$^e$, —NR$^d$C(O)NR$^d$R$^e$, —CR$^d$(N—OR$^e$), CF$_3$, and —OCF$_3$; wherein Cy is optionally substituted with one to four substituents independently selected from R$^c$ wherein:

R$^c$ is selected from the group consisting of halogen, amino, carboxy, C$_{1-4}$ alkyl, C$_{1-4}$ alkoxy, aryl, aryl-C$_{1-4}$ alkyl, hydroxy, CF$_3$, and aryloxy;

R$^d$ and R$^e$ are independently selected from hydrogen, alkyl, alkenyl, alkynyl, Cy and Cy-alkyl wherein alkyl, alkenyl, alkynyl and Cy are optionally substituted with one to four substituents independently selected from R$^c$; or R$^d$ and R$^e$ together with the atoms to which they are attached form a heterocyclic ring of 5 to 7 atoms and containing 0–2 additional heteroatoms independently selected from oxygen, sulfur and nitrogen; and R$^f$ and R$^g$ are independently selected from hydrogen, alkyl, Cy and Cy-alkyl; or R$^f$ and R$^g$ together with the carbon to which they are attached form a ring of 5 to 7 atoms containing 0–2 heteroatoms independently selected from oxygen, sulfur and nitrogen;

R$^b$ is selected from the group consisting of R$^a$ as defined above, alkyl, alkenyl, alkynyl, aryl-C$_{1-10}$ alkyl, heteroaryl-C$_{1-10}$ alkyl, wherein alkyl, alkenyl, alkynyl, aryl, heteroaryl are optionally substituted with a group independently selected from R$^c$;

Cy is cycloalkyl, heterocyclyl, aryl, or heteroaryl; and

R$^{10}$ is selected from the group consisting of —C(O)OR$^d$, —P(O)(OR$^d$)(OR$^e$), —P(O)(R$^d$)(OR$^e$), —S(O)$_m$OR$^d$, —C(O)NR$^d$R$^h$, and -5-tetrazolyl where:
R$^d$ and R$^e$ are as defined above;
R$^h$ is selected from the group consisting of hydrogen, alkyl, alkenyl, alkynyl, cyano, aryl, aryl-C$_{1-10}$ alkyl, heteroaryl, heteroaryl-C$_{1-10}$ alkyl, or —SO$_2$R$^i$ wherein alkyl, alkenyl, and alkynyl are optionally substituted with one to four substitutents independently selected from R$^a$; and aryl and heteroaryl are each optionally substituted with one to four substituents independently selected from R$^b$ where R$^a$ and R$^b$ are as defined above;
R$^i$ is selected from the group consisting of alkyl, alkenyl, alkynyl, and aryl wherein alkyl, alkenyl, alkynyl and aryl are each optionally substituted with one to four substituents independently selected from R$^c$;

m is an integer from 1 to 2; and n is an integer from 1 to 10; or pharmaceutically acceptable salts, individual isomer, mixtures of isomers, and prodrugs thereof.

In a second aspect, this invention provides a pharmaceutical composition comprising a therapeutically effective amount of a compound of Formula (I) and a pharmaceutically acceptable excipient.

In a third aspect, this invention provides a method of treatment of a disease in a mammal treatable by administration of an α4β7 receptor antagonist, comprising administration of a therapeutically effective amount of a compound of Formula (I) or its pharmaceutically acceptable salt.

DETAILED DESCRIPTION OF THE INVENTION

Definitions

Unless otherwise stated, the following terms used in the, specification and claims have the meanings given below:

"Alkyl" means a linear or branched saturated monovalent hydrocarbon radical of one to ten carbon atoms, more preferably one to six carbon atoms. This term is exemplified by groups such as methyl, ethyl, propyl, 2-propyl, tert-butyl, n-heptyl, octyl and the like.

"Alkylene" means a linear or branched saturated divalent hydrocarbon radical of one to ten carbon atoms, preferably one to six carbon atoms. This term is exemplified by groups such as methylene, ethylene, propylene, 2-methylpropylene, pentylene, and the like.

"Alkenyl" means a linear or branched monovalent hydrocarbon radical of two to ten carbon atoms, preferably two to six carbon atoms, containing at least one double bond, preferably one or two double bond(s). This term is exemplified by groups such as ethenyl, propenyl, and the like.

"Alkenylene" means a linear or a branched monovalent hydrocarbon radical of two to ten carbon atoms, preferably two to six carbon atoms, containing at least one double bond. This term is exemplified by groups such as ethenylene, 2-propenylene, and the like.

"Alkynyl" means a linear or branched monovalent hydrocarbon radical of two to ten carbon atoms, preferably two to six carbon atoms, containing at least one triple bond, preferably one or two triple bond(s). This term is exemplified by groups such as ethynyl, propynyl, and the like.

"Alkynylene" means a linear or a branched monovalent hydrocarbon radical of two to ten carbon atoms, preferably two to six carbon atoms, containing at least one triple bond. This term is exemplified by groups such as ethynylene, 2-propynylene, and the like.

"Halo" or "halogen" refers to fluoro, chloro, bromo and iodo and preferably is either chloro or bromo.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroarl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-subsgtituted heterocyclic where R is hydrogen or alkyl, mono- and di-alkylamnino, mono- and, di-(substituted alkyl)amino, mono- and di-aryl amino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different sub subtituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloaflkyl, —SO$_2$-aryl, —SO$_2$-substituted aryl, —SO$_2$-heteroaryl, —SO$_2$-substituted heterdaryl, —SO$_2$-heterocyclic, —SO$_2$-substituted heterocyclic and —SO$_2$NRR where R is hydrogen or alkyl.

"Substituted alkylene" refers to an alkyl group, preferably of from 1 to 10 carbon atoms, having from 1 to 5 substituents selected from the group consisting of alkoxy, substituted alkoxy, acyl, acylamino, thiocarbonylanno, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocydloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioatkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloallkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl; —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen; or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsyrmetric di-substituted amines having different substituents selected from alkyl, substituted alkyl, aryl, substituted aryl, heteroaryl, substituted heteroaryl, heterocyclic and substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioatkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkyl" refers to cyclic alkyl groups of from 3 to 8 carbon atoms having a single cyclic ring which is optionally fused to an aryl, heteroaryl, substituted aryl, or substituted heteroaryl ring e.g., cyclopropyl, cyclobutyl, cyclopentyl, cyclooctyl and the like.

"Cycloalkenyl" refers to cyclic alkenyl groups of from 3 to 8 carbon atoms having single or multiple unsaturation but which are not aromatic.

"Substituted cycloalkyl" and "substituted cycloalkenyl" refer to a cycloalkyl and cycloalkenyl groups, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which may optionally be condensed to a heteroaryl, substituted heteroaryl, cycloalkyl, or heterocyclic ring (e.g., 2-benzoxazolinone, 2H-1,4-benzoxazin-3(4H)-one-7yl, and the like). Preferred aryls include phenyl and naphthyl.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryl" refers to an aromatic carbocyclic group of from 2 to 10 carbon atoms and 1 to 4 heteroatoms selected from oxygen, nitrogen and sulfur within the ring. The heteroaryl group may optionally be fused to an aryl, substituted aryl, or heterocyclic ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, amninoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more of the rings can be aryl or heteroaryl.

"Substituted heterocyclic" refers to heterocycle groups which are substituted with from 1 to 3 substituents selected from the group consisting of oxo (═O), thioxo (═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuiranyl, and the like.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Alkenyloxy" refers to the group "alkenyl-O—".

"Substituted alkenyloxy" refers to the group "substituted alkenyl-O—".

"Acyl" refers to the groups —C(O)—H, —C(O)-alkyl, —C(O)-substituted alkyl, —C(O)-alkenyl, —C(O)-substituted alkenyl, —C(O)-alkynyl, —C(O)-substituted alkynyl, —C(O)-cycloalkyl, —C(O)-substituted cycloalkyl, —C(O)-aryl, —C(O)-substituted aryl, —C(O)-heteroaryl, —C(O)-substituted heteroaryl, —C(O)-heterocyclic, and —C(O)-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups —OC(O)-alkyl, —OC(O)-substituted alkyl, —OC(O)-alkenyl, —OC(O)-substituted alkenyl, —OC(O)-alkynyl, —OC(O)-substituted alkynyl, —OC(O)-aryl, —OC(O)-substituted aryl, —OC(O)-cycloalkyl, —OC(O)-substituted cycloalkyl, —OC(O)-heteroaryl, —OC(O)-substituted heteroaryl, —OC(O)-heterocyclic, and —OC(O)-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Carboxyalkyl", "carboxy-substituted alkyl", "carboxy cycloalkyl", "carboxy-substituted cycloalkyl", "carboxy aryl", "carboxy-substituted aryl", "carboxy heteroaryl", "carboxy-substituted heteroaryl", "carboxy heterocyclic", "carboxy -substituted heterocyclic", refers to the groups —C(O)O—R where R is alkyl, substituted alkyl, cycloalkyl, substituted cycloalkyl, aryl, substituted aryl, heteroaryl, substituted heteroaryl, heterocyclic and substituted heterocyclic are as defined herein.

"Amidino" refers to the group $H_2NC(=NH)$— and the term "alkylamidino" refers to compounds having 1 to 3 alkyl groups (e.g., alkylHNC(=NH)—).

"Thioamidino" refers to the group RSC(=NH)— where R is hydrogen or alkyl.

"Aminoacyl" refers to the groups —NRC(O)alkyl, —NRC(O)-substituted alkyl, —NRC(O)-cycloalkyl, —NRC(O)-substituted cycloalkyl, —NRC(O)-alkenyl, —NRC(O)-substituted alkenyl, —NRC(O)-alkynyl, —NRC(O)-substituted alkynyl, —NRC(O)-aryl, —NRC(O)-substituted aryl, —NRC(O)-heteroaryl, —NRC(O)-substituted heteroaryl, —NRC(O)-heterocyclic, and —NRC(O)-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Cycloalkoxy" refers to —O-cycloalkyl groups.

"Substituted cycloalkoxy" refers to —O-substituted cycloalkyl groups.

"Clcloalkenyloxy" refers to —O-cycloalkenyl groups.

"Substituted cycloalkenoxy" refers to —O-substituted cycloalkenyl groups.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alcynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heteroaryloxy" refers to the group —O-heteroaryl and "substituted heteroaryloxy" refers to the group —O-substituted heteroaryl.

"Heterocyclyloxy" refers to the group —O-heterocyclic and "substituted heterocyclyloxy" refers to the group —O-substituted heterocyclic.

"Lactam " refers to a ring containing the group —C(O)—NR— as part of the ring, where R is alkyl, substituted alkyl, aryl, substituted aryl, cycloalkyl, substituted cycloalkyl, heterocyclic, substituted heterocyclic, heteroaryl, substituted heteroaryl and —C(O)OR.

"Thiol" refers to the group —SH.

"Thioaikyl" refers to the groups —S-alkyl

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Pro-drugs" means any compound which releases an active parent drug according to formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, carboxy, or sulfhydryl group in compound (I) is bonded to any group that may be cleaved in vivo to regenerate the free hydroxyl, amino, carboxy, or sulfhydryl group, respectively. Examples of prodrugs include, but are not limited to esters (e.g., acetate, formate, and benzoate derivatives), in compounds of Formula (I), and the like.

"Optional" or "optionally" means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the C carbon atom to which the —Q—Ar$^1$ group is attached in a compound of Formula (I) is an asymmetric center and therefore the compound of formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable salt" refers to pharmaceutically acceptable salts of a compound of Formula I which salts are derived from a variety of organic and inorganic counter. ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Representative Compounds of Formula (I)

I. Representative compounds of Formula (I) where Q is —CH$_2$—; A together with —CH— and W forms cyclohexane, Z is —O—, R$^2$ and R$^4$ are hydrogen, R$^{10}$ is —COOH, and other groups are as defined below are:

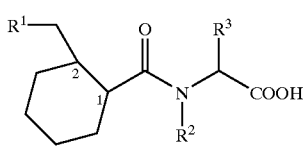

(I)

| CPD # | Stereochem. at C$^1$ & C$^2$ | R$^1$ | R$^3$ |
|---|---|---|---|
| 1 | (1S, 2R) | phenyl | 4-[N(CH$_3$)$_2$C(O)O]C$_6$H$_5$CH$_2$— |
| 2 | (1S, 2R) | phenyl | 4-(thiomorpholin-4-yl-carbonyloxy)benzyl |

-continued (I)

| CPD # | Stereochem. at $C^1$ & $C^2$ | $R^1$ | $R^3$ |
|---|---|---|---|
| 3 | (1S, 2R) | 3,5-difluoro-phenyl | 4-(1,1-dioxothiomorpholin-1-yl)benzyl |
| 4 | (1S, 2R) | 3,5-difluoro-phenyl | 4-[N(CH$_3$)$_2$C(O)O]C$_6$H$_5$CH$_2$— |
| 5 | (1S, 2R) | 3,4-difluoro-phenyl | 4-[N(CH$_3$)$_2$C(O)O]C$_6$H$_5$CH$_2$— |
| 6 | (1S, 2R) | pyridin-3-yl | 4-[N(CH$_3$)$_2$C(O)O]C$_6$H$_5$CH$_2$— |
| 7 | (1S, 2R) | pyridin-4-yl | 4-[N(CH$_3$)$_2$C(O)O]C$_6$H$_5$CH$_2$— |

II. Representative compounds of Formula (I) where Q is —CH$_2$—, A together with —CH— and W forms 2-oxazolidone, Z is —O—, $R^2$ and $R^4$ are hydrogen, $R^{10}$ is —COOH, and other groups are as defined below are:

(I)

| CPD # | Stereochem. at $C^4$ & $C^5$ | $R^1$ | $R^3$ |
|---|---|---|---|
| 1 | (4S, 5R) | phenyl | 4-[N(CH$_3$)$_2$C(O)O]C$_6$H$_5$CH$_2$— |
| 2 | (4S, 5R) | phenyl | benzyl |

PREFERRED EMBODIMENTS

While the broadest definition of this invention is set forth in the Summary of the Invention, certain compounds of Formula (I) are preferred.

Group I

1. A preferred group of compounds of Formula (I) is that wherein:
   A together with —CH— and W forms a cycloalkyl group, preferably cyclopropyl, cyclopentyl, or cyclohexyl, most preferably cyclohexyl.
2. Another preferred group of compounds is that wherein:
   A together with —C(H)$_p$— and W forms a heterocyclic or substituted heterocyclic group, preferably 2-oxo-oxazolidine.

Within this preferred group (I)(1–2), a more preferred group of compounds is that wherein:
Z is —O—;
$R^2$ and $R^4$ are hydrogen; and
$R^{10}$ is —COOR$^d$ where R$^d$ is hydrogen or alkyl, preferably hydrogen.

Within these preferred and more preferred groups, and even more preferred group of compounds is that wherein:
Q is alkylene, —CH(OH)—, or —CO—; preferably methylene; and
$R^3$ is:
(a) -(alkylene)-Ar—R$^6$, preferably —CH$_2$—Ar—O—CONR$^7$R$^8$ wherein Ar is aryl, and R$^7$ and R$^8$ are independently selected from the group consisting of hydrogen, alkyl, substituted alkyl, cycloalkyl, heterocyclic, or substituted heterocyclic; or R$^7$ and R$^8$ are joined to form a heterocycle or substituted heterocycle, preferably 3-[(CH$_3$)$_2$NC(O)O-]benzyl;
4-[(CH$_3$)$_2$NC(O)O-]benzyl;
4-[piperidin-1-yl)C(O)-]benzyl;
4-[(piperidin-4-yl)C(O)O-]benzyl;
4-[(1-methylpiperidin-4-yl)C(O)O-]benzyl;
4-[(4-hydroxypiperidin-1-yl)C(O)O-]benzyl;
4-[(4-formyloxypiperidin-1-yl)C(O)O-]benzyl;
4-[(4-ethoxycarbonylpiperidin-1-yl)C(O)O-]benzyl;
4-[(4-carboxypiperidin-1-yl)C(O)O-]benzyl;
4-[(3-hydroxymethylpiperidin-1-yl)C(O)O-]benzyl;
4-[(4-hydroxymethylpiperidin-1-yl)C(O)O-]benzyl;
4-[(4-phenyl-1-Boc-piperidin-4-yl)C(O)O-]benzyl;
4-[(4-piperidon-1-yl ethylene ketal)C(O)O-]benzyl;
4-[(piperazin-4-yl)C(O)O-]benzyl;
4-[(4-Boc-piperazin-1-yl)C(O)O-]benzyl;
4-[(4-methylpiperazin-1-yl)C(O)O-]benzyl;
4-[(4-methylhomopiperazin-1-yl )C(O)O-]benzyl;
4-[(4-(2-hydroxyethylpiperazin-1-yl)C(O)O-]benzyl;
4-[(4-phenylpiperazin-1-yl)C(O)O-]benzyl;
4-[(4-pyridin-2-yl)piperazin-1-yl)C(O)O-]benzyl;
4-[(4-(4-trifluoromethylpyridin-2yl)piperazin-1-yl)C(O)O-]benzyl;
4-[(4-(pyrimidin-2-yl)piperazin-1-yl)C(O)O-]benzyl;
4-[(4-acetylpiperazin-1-yl)C(O)O-]benzyl;
4-[(4-benzoylpiperazin-1-yl)C(O)O-]benzyl;
4-[(4-(pyridin-4-ylcarbonyl)piperazin-1-yl)C(O)O-]benzyl;
4-[(4-(phenylNHCO-)piperazin-1-yl)C(O)O-]benzyl;
4-[(4-(phenylNHCS-)piperazin-1-yl)C(O)O-]benzyl;
4-[(4-methanesulfonylpiperazin-1-yl)C(O)O-]benzyl;
4-[(4-trifluoromethanesulfonylpiperazin-1-yl)C(O)O-]benzyl;
4-[(morpholin-4-yl)C(O)O-]benzyl;
3-nitro-4-[(morpholin-4-yl)C(O)O-]benzyl;
4-[(thiomorpholin-4-yl)C(O)O-]benzyl;
4-[(1,1-dioxothiomorpholin-4-yl)C(O)O-]benzyl;
4-[pyrroldin-1-yl)C(O)O-]benzyl;
4-[(2-methylpyrrolidin-1-yl)C(O)O-]benzyl;
4-[(2-methoxycarbonylpyrrolidin-1-yl)C(O)O-]benzyl;
4-[(2-hydroxymethylpyrrolidin-1-yl)C(O)O-]benzyl;
4-[(2-N,N-dimethylarinoethyl)(methyl)NC(O)O-]benzyl;
4-[(2-(N-methyl-N4-toluylsulfonylaminoethyl)(methyl)NC(O)O-]-benzyl;
4-[(2-morpholin-4-ylethyl)(methyl)NC(O)O-]benzyl;
4-[(2-hydroxyethyl)(methyl)NC(O)O-]benzyl;
4-[bis(2-hydroxyethyl)NC(O)O-]benzyl;
4-[(2-formyloxyethyl)(methyl)NC(O)O-]benzyl;
4-[(CH$_3$OCOCH$_2$)NHC(O)O-]benzyl;
4-[(2-(phenylNHCOO)ethyl]NHC(O)O-]benzyl;
3-chloro-4-[(CH$_3$)$_2$NC(O)O-]benzyl;
3-chloro-4-[(4-methylpiperazin-1-yl)C(O)O-]benzyl;
3-chloro-4-[(4-(pyridin-2-yl)piperazin-1-yl)C(O)O-]benzyl;
3-chloro-4-[(thiomorpholin-4-yl)C(O)O-]benzyl; and
3-fluoro-4-[(CH$_3$)$_2$NC(O)O-]benzyl; or (b) $R^3$ corresponds to the $R^6$ group (including the preferred embodiments) found in PCT Application No. WO 98/53817 which application is incorportated herein by reference in its entirety. Preferably $R^3$ is CH$_2$Ar$^2$—Ar$^1$.

Within these preferred, more, and even more preferred groups, particularly preferred group of compounds is that wherein:

$R^1$ is aryl or substituted aryl ring, preferably phenyl or substituted phenyl; or $R^1$ is heteroaryl or substituted heteroaryl ring.

Group II

Another preferred group of compounds is that wherein:

$R^3$ is:

(a) -(alkylene)-Ar—$R^6$, preferably —CH$_2$—Ar—O—CONR$^7$R$^8$ wherein Ar is aryl, and $R^7$ and $R^8$ are independently selected from the group consisting of hydrogen, alkyl, substituted alkyl, cycloalkyl, heterocyclic, or substituted heterocyclic; or $R^7$ and $R^8$ are joined to form a heterocycle or substituted heterocycle, preferably 3-[(CH$_3$)$_2$NC(O)O-]benzyl;
4-[(CH$_3$)$_2$NC(O)O-]benzyl;
4-[(piperidin-1-yl)C(O)O-]benzyl;
4-[(piperidin-4-yl)C(O)O-]benzyl;
4-[(1-methylpiperidin-4-yl)C(O)O-]benzyl;
4-[(4-hydroxypiperidin-1-yl)C(O)O-]benzyl;
4-[(4-formyloxypiperidin-1-yl)C(O)O-]benzyl;
4-[(4-ethoxycarbonylpiperidin-1-yl)C(O)O-]benzyl;
4-[(4-carboxypiperidin-1-yl)C(O)O-]benzyl;
4-[(3-hydroxymethylpiperidin-1-yl)C(O)O-]benzyl;
4-[(4-hydroxymethylpiperidin-1-yl)C(O)O-]benzyl;
4-[(4-phenyl-1-Boc-piperidin-4-yl)C(O)O-]benzyl;
4-[(4-piperidon-1-yl ethylene ketal)C(O)O-]benzyl;
4-[(piperazin-4-yl)C(O)O-]benzyl;
4-[(1-Boc-piperazin-4-yl)C(O)O-]benzyl;
4-[(4-methylpiperazin-1-yl)C(O)O-]benzyl;
4-[(4-methylhomopiperazin-1-yl)C(O)O-]benzyl;
4-[(4-(2-hydroxyethylpiperazin-1-yl)C(O)O-]benzyl;
4-[(4-phenylpiperazin-1-yl)C(O)O-]benzyl;
4-[(4-(pyridin-2-yl)piperazin-1-yl)C(O)O-]benzyl;
4-[(4-(4-trifluoromethylpyridin-2yl)piperazin-1-yl)C(O)O-]benzyl;
4-[(4-(pyrimidin-2-yl)piperazin-1-yl)C(O)O-]benzyl;
4-[(4-acetylpiperazin-1-yl)C(O)O-]benzyl;
4-[(4-benzoylpiperazin-1-yl)C(O)O-]benzyl;
4-[(4-(pyridin-4-ylcarbonyl)piperazin-1-yl)C(O)O-]benzyl;
4-[(4-(phenylNHCO-)piperazin-1-yl)C(O)O-]benzyl;
4-[(4-(phenylNHCS-)piperazin-1-yl)C(O)O-]benzyl;
4-[(4-methanesulfonylpiperazin-1-yl)C(O)O-]benzyl;
4-[(4-trifluoromethanesulfonylpiperazin-1-yl)C(O)O-]benzyl;
4-[(morpholin-4-yl)C(O)O-]benzyl;
3-nitro-4-[(morpholin-4-yl)C(O)O-]benzyl;
4-[(thiomorpholin-4-yl)C(O)O-]benzyl;
4-[(1,1-dioxothiomorpholin-4-yl)C(O)O-]benzyl;
4-[(pyrrolidin-1-yl)C(O)O-]benzyl;
4-[(2-methylpyrrolidin-1-yl)C(O)O-]benzyl;
4-[(2-methoxycarbonylpyrrolidin-1-yl)C(O)O-]benzyl;
4-[(2-hydroxymethylpyrrolidin-1-yl)C(O)O-]benzyl;
4-[(2-N,N-dimethylaminoethyl)(methyl)NC(O)O-]benzyl;
4-[(2-(N-methyl-N-4-toluylsulfonylaminoethyl)(methyl)NC(O)O-]-benzyl;
4-[(2-morpholin-4-ylethyl)(methyl)NC(O)O-]benzyl;
4-[(2-hydroxyethyl)(methyl)NC(O)O-]benzyl;
4-[bis(2-hydroxyethyl)NC(O)O-]benzyl;
4-[(2-formyloxyethyl)(methyl)NC(O)O-]benzyl;
4-[(CH$_3$OCOCH$_2$)NHC(O)O-]benzyl;
4-[(2-(phenylNHCOO)ethyl]NHC(O)O-]benzyl;
3-chloro-4-[(CH$_3$)$_2$NC(O)O-]benzyl;
3-chloro-4-[(4-methylpiperazin-1-yl)C(O)O-]benzyl;
3-chloro-4-[(4-(pyridin-2-yl)piperazin-1-yl)C(O)O-]benzyl;
3-chloro-4-[(thiomorpholin-4-yl)C(O)O-]benzyl; and
3-fluoro-4-[(CH$_3$)$_2$NC(O)O-]benzyl; or (b) $R^3$ corresponds to the $R^6$ group (including the preferred embodiments) found in PCT Application No. WO 98/53817 which application is incorportated herein by reference in its entirety. Preferably $R^3$ is —CH$_2$Ar$^2$—Ar$^1$; and $R^4$ is hydrogen.

Within this preferred group II a more preferred group of compounds is that wherein:

$R^2$ is hydrogen; and $R^{10}$ is —COOH.

Within these preferred and more preferred groups, an even more preferred group of compounds is that wherein:

Q is alkylene, preferably methylene;

$R^1$ is aryl or substituted aryl, preferably phenyl or substituted phenyl.

Within these preferred, more preferred and even more preferred groups, particularly preferred group of compounds is that wherein:

1. A together with —CH— and W forms a cycloalkyl group, preferably cyclopropyl, cyclopentyl, or cyclohexyl, most preferably cyclohexyl.

2. Another preferred group of compounds is that wherein:

Altogether with —CH— and W forms a heterocyclic or substituted heterocyclic group, preferably 2-oxo-oxazolidine.

Group III

Another preferred group of compounds is that wherein $R^1$ is aryl or substituted aryl; preferably phenyl; or $R^1$ is heteroaryl or substituted heteroaryl.

With these groups a more preferred group of compounds is that wherein X is —O—, $R^2$ and $R^4$ are hydrogen; and $R^{10}$ is —COOR$^d$ where $R^d$ is hydrogen or alkyl.

Within these preferred groups, a more preferred group of compounds is that wherein:

Q is alkylene, —CH(OH)—, or —CO—; preferably methylene; and $R^3$ is:

(a) -(alkylene)-Ar—$R^6$, preferably —CH$_2$—Ar—O—CONR$^7$R$^8$ wherein Ar is aryl, and $R^7$ and $R^8$ are independently selected from the group consisting of hydrogen, alkyl, substituted alkyl, cycloalkyl, heterocyclic, or substituted heterocyclic; or $R^7$ and $R^8$ are joined to form a heterocycle or substituted heterocycle, preferably 3-[(CH$_3$)$_2$NC(O)O-]benzyl;
4-[(CH$_3$)$_2$NC(O)O-]benzyl;
4-[(piperidin-1-yl)C(O)O-]benzyl;
4-[(piperidin-4-yl)C(O)O-]benzyl;
4-[(1-methylpiperidin-4-yl)C(O)O-]benzyl;
4-[(4-hydroxypiperidin-1-yl)C(O)O-]benzyl;
4-[(4-formyloxypiperidin-1-yl)C(O)O-]benzyl;
4-[(4-ethoxycarbonylpiperidin-1-yl)C(O)O-]benzyl;
4-[(4-carboxypiperidin-1-yl)C(O)O-]benzyl;
4-[(3-hydroxymethylpiperidin-1-yl)C(O)O-]benzyl;
4-[(4-hydroxymethylpiperidin-1-yl)C(O)O-]benzyl;
4-[(4-phenyl-1-Boc-piperidin-4-yl)C(O)O-]benzyl;
4-[(4-piperidon-1-yl ethylene ketal)C(O)O-]benzyl;
4-[(piperazin-4-yl)C(O)O-]benzyl;
4-[(1Boc-piperazin-4-yl)C(O)O-]benzyl;
4-[(4-methylpiperazin-1-yl)C(O)O-]benzyl;
4-[(4-methylhomopiperazin-1-yl)C(O)O-]benzyl;
4-[(4-(2-hydroxyethylpiperazin-1-yl)C(O)O-]benzyl;
4-[(4-phenylpiperazin-1-yl)C(O)O-]benzyl;
4-[(4-pyridin-2-yl)piperazin-1-yl)C(O)O-]benzyl;
4-[(4-(4-trifluoromethylpyridin-2yl)piperazin-1-yl)C(O)O-]benzyl;

4-[(4-pyrimidin-2-yl)piperazin-1-yl)C(O)O-]benzyl;
4-[(4-acetylpiperazin-1-yl)C(O)O-]benzyl;
4-[(4-benzoylpiperazin-1-yl)C(O)O-]benzyl;
4-[(4-(pyridin-4-ylcarbonyl)piperazin-1-yl)C(O)O-]benzyl;
4-[(4-(phenylNHCO-)piperazin-1-yl)C(O)O-]benzyl;
4-[(4-(phenylNHCS-)piperazin-1-yl)C(O)O-]benzyl;
4-[(4-methanesulfonylpiperazin-1-yl)C(O)O-]benzyl;
4-[(4-trifluoromethanesulfonylpiperazin-1-yl)C(O)O-]benzyl;
4-[(morpholin-4-yl)C(O)O-]benzyl;
3-nitro-4-[(morpholin-4-yl)C(O)O-]benzyl;
4-[(thiomorpholin-4-yl)C(O)O-]benzyl;
4-[(1,1-dioxothiomorpholin-4-yl)C(O)O-]benzyl;
4-[(pyrrolidin-1-yl)C(O)O-]benzyl;
4-[(2-methylpyrrolidin-1-yl)C(O)O-]benzyl;
4-[(2-methoxycarbonylpyrrolidin-1-yl)C(O)O-]benzyl;
4-[(2-hydroxymethylpyrrolidin-1-yl)C(O)O-]benzyl;
4-[(2-N,N-dimethylaminoethyl)(methyl)NC(O)O-]benzyl;
4-[(2-(N-methyl-N-4-toluylsulfonylaminoethyl)(methyl)NC(O)O-]-benzyl;
4-[(2-morpholin-4-ylethyl)(methyl)NC(O)O-]benzyl;
4-[(2-hydroxyethyl)(methyl)NC(O)O-]benzyl;
4-[bis(2-hydroxyethyl)NC(O)O-]benzyl;
4-[(2-formyloxyethyl)(methyl)NC(O)O-]benzyl;
4-[(CH$_3$OCOCH$_2$)NHC(O)O-]benzyl;
4-[(2-(phenylNHCOO)ethyl]NHC(O)O-]benzyl;
3-chloro-4-[(CH$_3$)$_2$NC(O)O-]benzyl;
3-chloro-4-[(4-methylpiperazin-1-yl)C(O)O-]benzyl;
3-chloro-4-[(4-(pyridin-2-yl)piperazin-1-yl)C(O)O-]benzyl;
3-chloro-4-[(thiomorpholin-4-yl)C(O)O-]benzyl; and
3-fluoro-4-[(CH$_3$)$_2$NC(O)O-]benzyl.

Within these preferred, more preferred groups, an even more preferred group of compounds is that wherein:
1. A together with —CH— and W forms a cycloalkyl group, preferably cyclopropyl, cyclopentyl, or cyclohexyl, most preferably cyclohexyl.
2. Another preferred group of compounds is that wherein:
   A together with —CH— and W forms a heterocyclic or substituted heterocyclic group, preferably 2-oxo-oxazolidine.

General Synthesis

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis,* Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Synthesis of compounds of Formula (I) is described in Schemes A and B below.

Compounds of Formula (I) where Z is —O— and other groups are as defined in the Summary of the Invention are prepared as shown in Scheme A below.

Scheme A

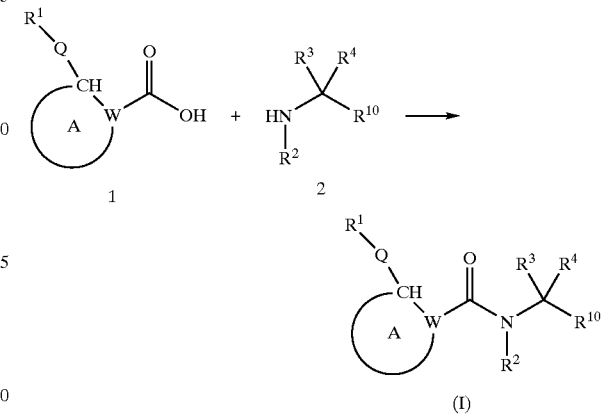

In general compounds of Formula (I) where Z is —O— and other groups are as defined in the Summary of the Invention are prepared by coupling a carboxylic acid derivative of formula 1 where R$^1$, Q, A and W are as defined in the Summary of the Invention with an α-amino acid derivative of formula 2 where R$^2$, R$^3$, and R$^{10}$ are as defined herein, under conventional amino acid coupling conditions. In some case, conventional protecting groups may be required to prevent undesired side reactions, such as where R$^{10}$ is —COOH. In such cases, esters, i.e., where R$^{10}$ is —COOR where R is alkyl, will typically be employed.

This coupling reaction is typically conducted using well-known coupling reagents such as carbodiimides, BOP reagent (benzotriazol-1-yloxy-tris(dimethylamino) phosphohium hexafluorophosphonate) and the like. Suitable carbodiimides include, by way of example, dicyclohexylcarbodiimide (DCC), 1-(3-dimethylaminopropyl)-3-ethylcarbodiimide (EDC) and the like. If desired, polymer supported forms of carbodiimide coupling reagents may also be used including, for example, those described in *Tetrahedron Letters*, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting acid 1 with about 1 to about 2 equivalents of the coupling reagent and at least one equivalent, preferably about 1 to about 1.2 equivalents, of amino acid derivative 2 in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 h. Upon completion of the reaction, the compound of Formula (I) is recovered by conventional methods including neutralization, extraction, precipitation, chromatography, filtration, and the like.

Alternatively, acid 1 can be converted into an acid halide which is then coupled with amino acid derivative 2 to provide compounds of Formula (I). The acid halide of 1 can be prepared by contacting 1 with an inorganic acid halide, such as thionyl chloride, phosphorous trichloride, phosphorous tribromide or phosphorous pentachloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 h. A catalyst, such as N,N-dimethylformamide, may also be used in this reaction.

The acid halide of acid 1 is then contacted with at least one equivalent, preferably about 1.1 to about 1.5 equivalents, of amino acid derivative 2 in an inert diluent, such as dichloromethane, at a temperature ranging from about −70° C. to about 40° C. for about 1 to about 24 h. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, the compound of Formula (I) is recovered by conventional methods including neutralization, extraction, precipitation, chromatography, filtration, and the like.

Acids of formula 1 employed in the above described coupling reaction are either commercially available or they can be prepared from commercially available starting materials using conventional procedures and reagents. For example, compounds of formula 1 where (Q is —CO—, —CH$_2$—, or —CHOH) can be prepared from an anhydride of formula 3 as shown below.

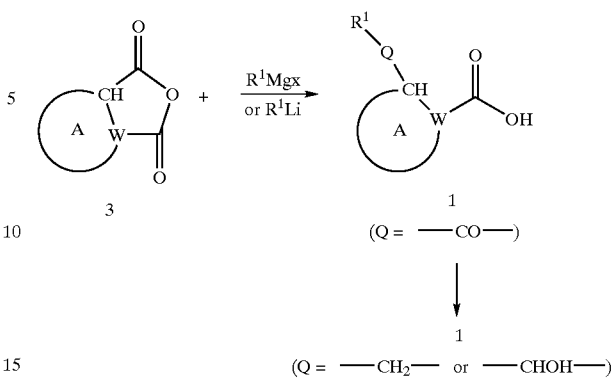

Compounds of formula 1 (where Q is —CO—) are prepared by reacting an anhydride of formula 3 where A and W are as defined in the Summary of the Invention, with an organicmetallic agent such as a Grignard reagent or an organic lithium reagent of formula R$^1$MgX or R$^1$Li respectively where R$^1$ is as defined in the Summary of the Invention. Suitable solvents for the reaction are aprotic organic solvents such as diethyl ether, tetrahydrofuran, and the like. The Grignard reagent and the organic lithium reagent are either commercially available or they can be prepared by methods well known in the art. For example, R$^1$Li can be prepared by treating an organic halide of formula R$^1$X where X is a halo group with an organic base such as butyllithium.

A compound of formula 1 (where Q is —CO—) can be converted to a corresponding compound of formula 1 (where Q is —CH$_2$— or —CHOH) by reduction of the carbonyl group. Suitable reducing agent for converting —CO— to —CHOH' are by treating them with suitable reducing agent such as sodium borohydride. Conversion of —CO— to —CH$_2$— can be achieved under standard catalytic hydrogenation reaction conditions.

Anhydrides of formula 3 are commercially available. For example, cis-1,2-cyclohexanedicarboxylic anhydride is commercially available.

The amino acid derivatives of formula 2 employed in the above reactions are either known compounds or compounds that can be prepared from known compounds by conventional synthetic procedures. For example, amino acid derivatives of formula 2 can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 h. The resulting C-alkylated malonate is then de-acetylated, hydrolyzed and decarboxylated by heating in aqueous hydrochloric acid at reflux for about 6 to about 12 h to provide the amino acid, typically as the hydrochloride salt.

Examples of amino acid derivatives of formula 2 suitable for use in the above reactions include, but are not limited to, L-tyrosine methyl ester, L-3,5-diiodotyrosine methyl ester, L-3-iodotyrosine methyl ester, β-(4-hydroxynaphth-1-yl)-L-alanine methyl ester, β-(6-hydroxynaphth-2-yl)-L-alanine methyl ester, L-4-(N,N-dimethylcarbamyloxy) phenylalanine ethyl ester and the like. If desired, of course, other esters or amides of the above-described compounds may also be employed.

For ease of synthesis, the compounds of Formula (I) are typically prepared as an ester, i.e., where $R^{10}$ is an —COOR (where R is alkyl or substituted alkyl, and the like). If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 12 h. Alternatively, benzyl esters may be removed by hydrogenolysis using a palladium catalyst, such as palladium on carbon. The resulting carboxylic acids may be coupled, if desired, to amines such as β-alanine ethyl ester, hydroxyamines such as hydroxylamine and N-hydroxysuccinimide, alkoxyamines and substituted alkoxyamines such as O-methylhydroxylamine and O-benzylhydroxylamine, and the like, using conventional coupling reagents and conditions as described above.

Scheme B

Alternatively, a compound of Formula (I) is prepared by coupling the acid 1 to a polymer-bound amino acid derivative of formula 5: where $R^2$, $R^3$ and $R^4$ are as defined herein, and P represents a polymer or resin. Polymer-bound amino acids are commercially available or can be prepared by

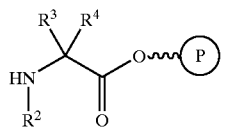

conventional procedures. Using the coupling procedures described above, compounds of Formula (I) can be coupled to polymer-bound amino acid derivative 5 and then cleaved from the polymer to provide compounds of Formula (I). Methods for preparing, coupling and cleaving polymer-bound amino acids are well known. Such methods are described, for example, in International Publication Number WO 98/53814, published Dec. 3, 1998, the disclosure of which is incorporated herein by reference in its entirety.

As will be apparent to those skilled in the art, other functional groups present on any of the substituents of the compounds of Formula (I), in addition to the carbamate-type functionality, can be readily modified or derivatized either before or after the above-described synthetic reactions using well-known synthetic procedures. For example, a nitro group present on a substituent of a compound of Formula (I) or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 h in an inert diluent, such as methanol. Compounds having a nitro group on the $R^1$ substituent can be prepared, for example, by using a 4-nitrobenzene derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 h in an acidic diluent, such as a mixture of methanol and aqueous hydrochloric acid.

Additionally, when the $R^1$ substituent of a compound of Formula (I) or an intermediate thereof contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on the $R^1$ substituent may be prepared, for example, by reduction of the corresponding nitro compound as described above.

By way of illustration, a compound of Formula (I) or an intermediate thereof having a substituent containing a primary or secondary amino group, such as where $R^1$ is 4-aminophenyl group, can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris (dimethylamino)-phosphonium hexafluorophosphonate) and the like, in an inert diluent, such as dichloromethane, chloroform, acetonitrile, tetrahydrofuran, N,N-dimethylformamide and the like, at a temperature ranging from about 0° C. to about 37° C. for about 4 to about 24 h. Preferably, a promoter, such as N-hydroxysuccinimide, 1-hydroxy-benzotriazole and the like, is used to facilitate the acylation reaction.

Alternatively, a compound of Formula (I) or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about of about −70° C. to about 40° C. for about 1 to about 24 h. If desired, an acylation catalyst such as 4-(N,N-dimethylamino)-pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoro-methylbenzoyl chloride, isonicotinoyl chloride, nicotinoyl chloride, picolinoyl chloride, acetic anhydride, succinic anhydride, and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of Formula (I) or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride, and the like. Similarly, sulfamoyl chlorides, such as dimethylsulfamoyl chloride, can be used to provide sulfamides (e.g., >N—$SO_2$—N<).

Additionally, a primary and secondary amino group present on a substituent of a compound of Formula (I) or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 h. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate, fluorescein isothiocyanate (isomer I) and the like.

Furthermore, when a compound of Formula (I) or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 h. Aldehydes and ketones suitable for use in this reaction include, by way of example, benzaldehyde, 4-chloro-benzaldehyde, valeraldehyde and the like.

In a similar manner, when a compound of Formula (I) or an intermediate thereof has a substituent containing a hydroxyl group, the hydroxyl group can be further modified or derivatized either before or after the above coupling reactions to provide, by way of example, ethers, carbamates and the like. Compounds having a hydroxyl group on the $R^3$ substituent, for example, can be prepared using an amino acid derivative derived from tyrosine and the like in the above-described reactions.

By way of example, a compound of Formula (I) or an intermediate thereof having a substituent containing a hydroxyl group, such as where $R^1$ is a (4-hydroxyphenyl) methyl group, can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 h. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino) ethyl chloride, 3-(N,N-ethylamino)propyl chloride, 3-(N-benzyl-N-methylamino)propyl chloride, N-(2-chloroethyl) morpholine, 2-(hexamethyleneimino)ethyl chloride, 3-(N-methylpiperazine)propyl chloride, 1-(3-chlorophenyl)-4-(3-chloropropyl)piperazine, 2-(4-hydroxy-4-phenylpiperidine) ethyl chloride, N-tert-butyloxycarbonyl-3-piperidinemethyl tosylate, and the like.

Alternatively, a hydroxyl group present on a substituent of a compound of Formula (I) or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 h. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 h to provide the O-alkylated product.

In a similar manner, a compound of Formula (I) or an intermediate thereof containing an aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25 ° C. to about 10° C. The salt is then treated with about 1.1 to about 1.5 equivalents of cuprous bromide dimethyl sulfide complex at a temperature ranging from about 10° C .to about 30° C. for about 0.5 to about 2.0 h, followed by about 1.1 to about 1.5 equivalents of an aryl iodide, such as sodium 2-iodobenzoate and the like. The reaction is then heated to about 70° C. to about 150° C. for about 2 to about 24 h to provide the diaryl ether.

Additionally, a hydroxy-containing compound can also be readily derivatized to form a carbamate. In one method for preparing such carbamates, a hydroxy compound of Formula (1) or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 h. Treatment of the resulting carbonate with an excess, preferably about 2 to about 5 equivalents, of a trialkylamine, such as triethylamine, for about 0.5 to 2 h, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25 ° C. to about 70° C. for about 2 to about 72 h. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of Formula (I) or an intermediate thereof contains a primary or secondary hydroxyl group, such hydroxyl groups can be readily converted into a leaving group arid displaced to form, for example, amines, sulfides and fluorides. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 h to provide the corresponding azido compound. The azido group can then be reduced by, for example, hydrogenation using a palladium on carbon catalyst to provide the amino (—NH$_2$) compound.

Similarly, a tosylate group can be readily displaced by a thiol to f6rm a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 h affords the corresponding fluoro compound.

Furthermore, a compound of Formula (I) or an intermediate thereof having a substituent containing an iodoaryl group, for example, when R$^3$ is a (4-iodophenyl)methyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra (triphenylphosphine), in an inert diluent, such as tetrahydrofuran, at a temperature ranging from about 24° C. to about 30° C. until reaction completion. This reaction is further described, for example, in Rieke, *J. Org. Chem.* 1991, 56, 1445. Additional methods for preparing biaryl derivatives are disclosed in International Publication Number WO 98/53817, published Dec. 3, 1998, the disclosure of which is incorporated herein by reference in its entirety.

In some cases, the compounds of Formula (I) or intermediates thereof may contain substituents having one or more sulfur atoms. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about –50° C. to about 75° C. for about 1 to about 24 h. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, "*Advanced Organic Chemistry*", 4th Ed., pp. 1201–1202, Wiley Publisher, 1992.

Other procedures and reaction conditions for preparing the compounds of this invention are described in the examples set forth below.

Pharmaceutical Formulations and Administration

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of Formula (I) above associated with pharmaceutically acceptable carriers. In. making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention can be employed to bind $\alpha_4\beta_7$ integrin in biological samples and, accordingly have utility in, for example, assaying such samples for $\alpha_4\beta_7$ integrin. In such assays, the compounds can be bound to a solid support and the $\alpha_4\beta_7$ integrin sample added thereto. The amount of $\alpha_4\beta_7$ integrin in the sample can be determined by conventional methods such as use of a sandwich ELISA assay. Alternatively, labeled $\alpha_4\beta_7$ integrin can be used in a competitive assay to measure for the presence of $\alpha_4\beta_7$ integrin in the sample. Other suitable assays are well known in the art.

In addition, certain of the compounds of this invention inhibit, in vivo, adhesion of leukocytes to endothelial cells and epithelial cells in mucosal organs mediated by $\alpha_4\beta_7$ integrin and, accordingly, can be used in the treatment of diseases mediated by $\alpha_4\beta_7$ integrin. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The biological activity of the compounds identified above may be assayed in a variety of systems. For example, a compound can be immobilized on a solid surface and adhesion of cells expressing $\alpha_4\beta_7$ integrin can be measured. Using such formats, large numbers of compounds can be screened. Cells suitable for this assay include any leukocytes known to express $\alpha_4\beta_7$ integrin such as memory T cells and eosinophils. A number of leukocyte cell lines can also be used, examples include RPMI-8866.

The test compounds can also be tested for the ability to competitively inhibit binding between $\alpha_4\beta_7$ integrin and MAdCAM-1, or between $\alpha_4\beta_7$ integrin and a labeled compound known to bind $\alpha_4\beta_7$ integrin such as a compound of this invention or antibodies to $\alpha_4\beta_7$ integrin. In these assays, the MAdCAM-1 can be immobilized on a solid surface. MAdCAM-1 may also be expressed as a recombinant fusion protein having an Ig tail (e.g., IgG Fc) so that binding to $\alpha_4\beta_7$ integrin may be detected in an immunoassay. Alternatively, MAdCAM-1 expressing cells, such as activated endothelial cells or MAdCAM-1 transfected fibroblasts can be used.

As discussed above, both $\alpha_4\beta_7$ and $\alpha_4\beta_1$ can mediate adhesion to VCAM-1 and to fibronectin. For assays which measure the ability to block adhesion to VCAM-1 and to fibronectin, the assays described in International Patent Application Publication No. WO US98/15324 are particularly preferred. This application is incorporated herein by reference in its entirety.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3H$, $^{125}I$, $^{35}S$, $^{14}C$, or $^{32}P$ labelled compounds or the like. Non-radioactive labels include ligands which bind to labelled antibodies, fluorophores, chemiluminescent agents, enzymes and antibodies which can serve as specific binding pair members for a labelled ligand. The choice of label depends on sensitivity required, ease of conjugation with the compound, stability requirements, and available instrumentation.

Appropriate in vivo models for demonstrating efficacy in treating inflammatory responses include EAE (experimental autoimmune encephalomyelitis) in mice, rats, guinea pigs or primates, as well as other inflammatory models dependent upon $\alpha 4$ integrins.

Compounds having the desired biological activity may be modified as necessary to provide desired properties such as improved pharmacological properties (e.g., in vivo stability, bio-availability), or the ability to be detected in diagnostic applications. For instance, inclusion of one or more D-amino acids in the sulfonamides of this invention typically increases in vivo stability. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83–93).

For diagnostic purposes, a wide variety of labels may be linked to the compounds, which may provide, directly or indirectly, a detectable signal. Thus, the compounds of the subject invention may be modified in a variety of ways for a variety of end purposes while still retaining biological activity. In addition, various reactive sites may be introduced at the terminus for linking to particles, solid substrates, macromolecules, or the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing $\alpha_4\beta_7$ integrin. The compounds of this invention can also be used for isolating or labeling such cells. In addition, as mentioned above, the compounds of the invention can be used to assay for potential inhibitors of $\alpha_4\beta_7$ integrin/MAdCAM-1 interactions.

For in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic imaging can be used. Usually gamma- and positron-emitting radioisotopes are used for camera imaging and paramagnetic isotopes are used for MRI. Thus, the compounds can be used to monitor, the course of amelioration of an inflammatory response in an individual. By measuring the increase or decrease in lymphocytes expressing $\alpha_4\beta_7$ integrin it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis, myocardial ischemia, and inflammatory bowel disease (including Crohn's disease and ulcerative colitis). In preferred embodiments the pharmaceutical compositions are used to treat inflammatory brain disorders, such as multiple sclerosis (MS), viral meningitis and encephalitis.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993).

It is contemplated that compounds of this invention can be used in the treatment of organ or graft rejection mediated by $\alpha_4\beta_7$4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8$^+$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420–425 (1996); Georczynski et al., *Immunology* 87, 573–580 (1996); Georcyznski et al., *Transplant. Immunol.* 3, 55–61 (1995); Yang et al., *Transplantation* 60, 71–76 (1995); Anderson et al., *APMIS* 102, 23–27 (1994).

A related use for compounds of this invention which bind to $\alpha_4\beta_7$ is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers.

Pharmaceutical compositions of the invention are suitable for use in a variety of drug delivery systems. Suitable formulations for use in the present invention are found in *Remington's Pharmaceutical Sciences,* Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 500 µg per kilogram body weight, preferably about 100 µg to about 300 µg per kilogram body weight. Suitable-dosage ranges for intranasal administration are generally about 0.1 pg to 1 mg per kilogram body weight. Effective doses can be extrapolated from dose-response curves derived from in vitro or animal model test systems.

Compounds of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$ and $\alpha_4\beta_7$ are preferred in this invention). Accordingly, compounds of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\alpha_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.,* 188(11) 2187–2191(1998). Compounds that bind $\alpha_e\beta_7$ integrin are also useful for the treatment of systemic lupus erythematosus (see, for example, M. Pang et al., *Arthritis Rheum.* 41(8), 1456–1463 (1998)); Crohn's disease, ulcerative colitis and infammatory bowel disease (IBD) (see, for example, D. Elewaut et al., *Scand J. Gastroenterol.* 33(7) 743–748 (1998)); Sjogren's syndrome (see, for example, U. Kroneld et al., *Scand J. Gastroenterol,* 27(3), 215–218 (1998)); and rheumatoid arthritis (see, for example, *Scand J. Gastroenterol.* 44(3), 293–298 (1996)). And compounds that bind $\alpha_6\beta_1$ may be useful in preventing fertilization (see, for example, H. Chen et al., *Chem. Biol.* 6, 1–10 (1999)).

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| aq or aq.= | aqueous |
| bd= | broad doublet |
| bm= | broad multiplet |
| bs= | broad singlet |
| Boc= | N-tert-butoxylcarbonyl |
| Boc$_2$O= | di-tert-butyl dicarbonate |
| BOP= | benzotriazol-1-yloxy-tris(dimethylamino)phosphonium hexafluorophosphate |
| CH$_2$Cl$_2$= | dichloromethane |
| d= | doublet |
| dd= | doublet of doublets |
| dt= | doublet of triplets |
| DMAP= | 4-N,N-dimethylaminopyridine |
| DMF= | N,N-dimethylformamide |
| Et$_2$O= | diethyl ether |
| EtOAc= | ethyl acetate |
| g= | grams |
| h= | hour |
| H$_2$O= | water |
| HCl= | hydrochloric acid |
| HOBT= | 1-hydroxybenzotriazole hydrate |
| hr= | hour |
| K$_2$CO$_3$= | potassium carbonate |
| L= | liter |
| m= | multiplet |
| MgSO$_4$= | magnesium sulfate |
| mL= | milliliter |
| mm= | millimeter |
| mM= | millimolar |
| NaCl= | sodium chloride |
| Na$_2$CO$_3$= | sodium carbonate |
| NaHCO$_3$= | sodium bicarbonate |
| NaOH= | sodium hydroxide |
| q= | quartet |
| quint.= | quintet |
| rt= | room temperature |
| s= | singlet |
| sat.= | saturated |
| t= | triplet |
| TFA= | trifluoroacetic acid |
| THF= | tetrahydrofuran |
| TLC or tlc= | thin layer chromatography |

Synthetic Examples

The following Methods may be used to prepare the compounds of this invention.

Method A

Methyl Ester Preparation Procedure

Amino acid methyl esters can be prepared using the method of Brenner and Huber *Helv. Chim. Acta* 1953, 36, 1109.

Method B

BOP Coupling Procedure

The desired ester was prepared by the reaction of a carboxylic acid (1 equivalent) with the appropriate amino acid ester or amino acid ester hydrochloride (1 equivalent), benzotriazol-1-yloxy-tris(dimethylamino)-phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method C

Hydrogenation Procedure I

Hydrogenation was performed using 10% palladium on carbon (10% by weight) in methanol at 30 psi overnight. The mixture was filtered through a pad of Celite and the filtrate concentrated to yield the desired compound.

Method D

Hydrolysis Procedure I

To a chilled (0° C.) THF/H$_2$O solution (2:1, 5–10 mL) of the appropriate ester was added LiOH (or NaOH) (0.95 equivalents). The temperature was maintained at 0° C. and the reaction was complete in 1–3 hours. The reaction mixture was extracted with ethyl acetate and the aqueous phase was lyophilized resulting in the desired carboxylate salt.

Method E

Ester Hydrolysis Procedure II

To a chilled (0° C.) THF/H$_2$O solution (2:1, 5–10 mL) of the appropriate ester was added LiOH (1.1 equivalents). The temperature was maintained at 0° C. and the reaction was complete in 1–3 hours. The reaction mixture was concen-

Method F

Ester Hydrolysis Procedure III

The appropriate ester was dissolved in dioxane/H$_2$O (1:1) and 0.9 equivalents of 0.5 N NaOH was added. The reaction was stirred for 3–16 hours and then concentrated. The resulting residue was dissolved in H$_2$O and extracted with ethyl acetate. The aqueous phase was lyophilized to yield the desired carboxylate sodium salt.

Method G

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in Et$_2$O and reconcentrated. This procedure was repeated and the resulting solid was placed under high vacuum overnight.

Method H tert-Butyl Ester Hydrolysis Procedure I

The tert-butyl ester was dissolved in CH$_2$Cl$_2$ and treated with TFA. The reaction was complete in 1–3 hr at which time the reaction mixture was concentrated and the residue dissolved in H$_2$O and lyophilized to yield the desired acid.

Method I

EDC Coupling Procedure I

To a CH$_2$Cl$_2$ solution (5–20 mL) of a carboxylic acid (1 equivalent), the appropriate amino acid ester hydrochloride (1 equivalent), N-methyl-morpholine (1.1–2.2 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was poured into H$_2$O and the organic phase was washed with sat. NaHCO$_3$, brine, dried (MgSO$_4$ or Na$_2$SO$_4$), filtered and concentrated. The crude product was purified by column chromatography.

Method J

EDC Coupling Procedure II

To a DMF solution (5–20 mL) of a carboxylic acid (1 equivalent), the appropriated amino acid ester hydrochloride (1 equivalent), Et$_3$N (1.1 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was partitioned between EtOAc and H$_2$O and the organic phase washed with 0.2 N citric acid, H$_2$O, sat. NaHCO$_3$, brine, dried (MgSO$_4$ or Na$_2$SO$_4$), filtered and concentrated. The crude product was purified by column chromatography or preparative TLC.

trated and the residue was taken up into H$_2$O and the pH adjusted to 2–3 with aqueous HCl. The product was extracted with ethyl acetate and the combined organic phase was washed with brine, dried over MgSO$_4$, filtered and concentrated to yield the desired acid.

Method K tert-Butyl Ester Hydrolysis Procedure II

The tert-butyl ester was dissolved in CH$_2$Cl$_2$ (5 mL) and treated with TFA (5 mL). The reaction was complete in 1–3 hours at which time the reaction mixture was concentrated and the residue dissolved in H$_2$O and concentrated. The residue was redissolved in H$_2$O and lyophilized to yield the desired product.

Method L

Carbamate Formation Procedure I

Into a reaction vial were combined 15.2 mmol, 1.0 eq. of the starting hydroxy compound (typically a tyrosine derivative) and 1.86 g (15.2 mmol, 1.0 eq) DMAP. Methylene chloride (50 mL), triethylamine (2.12 mL, 1.54 g, 15.2 mmol, 1.0 eq), and dimethylcarbamyl chloride (1.68 mL, 1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The work-up of the reaction solution was as follows: 50 mL EtOAc and 50 mL hexanes was added to the reaction mixture, and the resulting mixture was washed with 0.5 M citric acid (3×50 mL), water (2×50 mL),10% K$_2$CO$_3$ (2×50 mL), and sat. NaCl (1×50 mL); dried with MgSO$_4$, filtered and evaporated to afford the desired compound.

Method M

Carbamate Formation Procedure II

Into a reaction vial were combined 84.34 mmol (1.0 eq) of the starting hydroxy compound (typically a tyrosine derivative) and 17.0 g (84.34 mmol, 1.0 eq) 4-nitrophenyl chloroformate. Methylene chloride (700 mL) was added and the vial was capped with a septum. A nitrogen line was attached and the vial was immersed in a 4:1 water/ethanol dry ice slurry with stirring to cool to −15° C. Triethylamine (29.38 mL, 21.33 g, 210.81 mmol, 2.5 eq) was added over five minutes with stirring and the stirring was continued at −10 to −15 ° C. for 1 h. N-Methylpiperazine (9.35 mL, 8.45 g, 84.34 mmol, 1.0 eq) was added over three minutes with stirring and stirring was continued overnight while warning to room temperature. The reaction mixture was diluted with 700 mL hexanes and the resulting mixture was washed repeatedly with 10% K$_2$CO$_3$, until no yellow color (from 4-nitrophenol) is observed in the aqueous layer. The mixture was then washed with sat. NaCl, dried over anhydrous MgSO$_4$, filtered and evaporated. The residue was dissolved in 500 mL of ethanol and evaporated to remove triethylamine. The residue was again dissolved in 500 mL of ethanol and evaporated to remove triethylamine. The residue was then dissolved in 400 mL of ethanol and 600 mL of water was added with stirring to precipitate a solid or oil. If an oil if formed, the oil is stirred vigorously to induce it to solidify. The solid is then isolated by filtration. Dissolution, precipitation, and filtration are repeated once and the resulting solid is rinsed with water to remove traces of yellow color. The solid is then subjected to high vacuum until the mass remains constant thereby affording the desired carbamyloxy compound.

Method N

Synthesis of (1S,2R)-2-(3,5-difluorobenzyl)cyclohexanecarboxylic acid

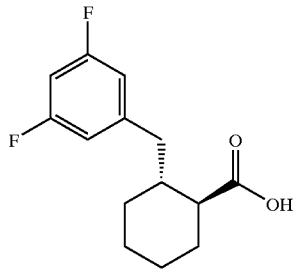

Step 1

A dry three-neck, round-bottom flask, equipped with a reflux condenser, was charged with magnesium turnings (1.89 g, 78 mmol) and iodine (0.131 g, 0.518 mmol). The apparatus was capped tightly with septa and purged with $N_2$, and then anhydrous diethyl ether (80 mL) was added by cannula. The reaction mixture was stirred for 2 h, during which time the iodine was consumed. The flask was cooled with an ice bath, and then 1-bromo-3,5-difluorobenzene (10 g, 51.8 mmol) was injected in portions with stirring. The ice bath was removed, and the reaction mixture was stirred for 1 h, during which time an exotherm was evident, and much of the Mg was consumed. The supernatant solution of the Grignard reagent was slowly transferred by cannula to a stirred solution of cis-1,2-cyclohexanedicarboxylic anhydride (7.98 g, 51.8 mmol) in anhydrous ether (120 mL), maintained at −78° C. under $N_2$. The resulting solution was stirred at −78° C. for 1 h, and then allowed to warm to 20° C. over 18 h. The reaction mixture was poured into 1M sulfuric acid (150 mL) and extracted with 200 mL hexanes. The organic layer was washed with sat. NaCl, dried over $MgSO_4$, filtered, and evaporated to give cis-2-(3,5-difluorophenylcarbonyl)-cyclohexanecarboxylic acid, as an oil, which was used immediately in the next step.

Step 2

Cis-2-(3,5-difluorophenylcarbonyl)cyclohexanecarboxylic acid was dissolved in 10% NaOH (250 mL) and the solution was stirred at 20° C. for 16 h. The aqueous solution was extracted with diethyl ether (100 mL), and then acidified with 1M hydrochloric acid. The resulting precipitate was collected, and recrystallized from $CH_2Cl_2$/hexanes, to give (1S,2R)-2-(3,5-difluorophenyl-carbonyl)cyclohexanecarboxylic acid as a white solid (4 g, 30% from cis-1,2-cyclohexanedicarboxylic anhydride).

Step 3

A mixture of (1S,2R)-2-(3,5-difluorophenylcarbonyl)cyclohexanecarboxylic acid (1 g, 3.7 mmol), 10% $Pd(OH)_2$ on carbon (1 g), tetrahydrofuran (10 mL) and acetic acid (0.5 mL) was shaken under hydrogen atmosphere at 50 psi for 96 h. The reaction mixture was filtered through Celite®, and filtrate and evaporated to give (1S,2R)-2-(3,5-difluorophenyl-methyl)cyclohexanecarboxylic acid, as a white solid (0.9 g, 95%).

Method O

Synthesis of (1S,2R)-2-(pyridin-4-ylmethyl)cyclohexanecarboxylic acid

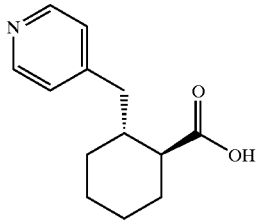

Step 1

4-Bromopyridine hydrochloride (10.05 g, 51.8 mmol) was treated with potassium carbonate (7.15 g, 51.8 mmol) in water (50 mL), and the resulting solution was saturated with sodium chloride. The 4-bromopyridine free base was extracted with diethyl ether, and the solution was stored under $N_2$ over 3 angstrom molecular sieves for 1 h. The 4-bromopyridine solution was slowly transferred by cannula to a stirred solution of 2.5 M butyllithium in hexane (21.2 mmL, 53 mmol) in anhydrous diethyl ether (100 mL), maintained at −78° C. under $N_2$. The reaction mixture was stirred for 30 min., and then a solution of cis-1,2-cyclohexanedicarboxylic anhydride (8.33 g, 54 mmol) in anhydrous tetrahydrofuran (150 mL) was added by cannula. The reaction mixture was stirred at −78° C. for 1 h and then allowed to warm to 20° C. The reaction mixture was quenched by addition of water (200 mL), and the aqueous layer was separated and acidified to pH=4 by addition of 6 M hydrochloric acid. The aqueous layer was saturated with sodium chloride and extracted with a (1:1) mixture of ethyl acetate and tetrahydrofuran (400 mL). The organic layer was washed with sat. NaCl, dried over $MgSO_4$, filtered, and evaporated to give cis-2-(4-pyridylcarbonyl)cyclohexanecarboxylic acid, as a solid, which was used immediately in the next step.

Step 2

Cis-2-(4-pyridylcarbonyl)cyclohexanecarboxylic acid was dissolved in 10% sodium hydroxide (300 mL) and stirred at 20° C. for 16 h. The aqueous solution was extracted with diethyl ether (200 mL) and then acidified to pH=4 by addition of 6 M hydrochloric acid. The resulting precipitate was collected and recrystallized from hot water, to give (1S,2R)-2-(4-pyridylcarbonyl)-cyclohexanecarboxylic acid, as a white solid (4.8 g, 40% from cis-1,2-cyclohexanedicarboxylic anhydride).

Step 3

A mixture of 8.5 M hydrochloric acid (10.5 mL), Zn (5.57 g, 85.2 mmol), and $HgCl_2$ (0.557 g, 2.1 mmol) was stirred for 15 min, and then (1S,2R)-2-(4-pyridylcarbonyl)cyclohexanecarboxylic acid (0.30 g, 1.3 mmol) was added. The reaction mixture was stirred at reflux for 20 h, and then diluted with 10% citric acid (75 mL), and then adjusted to pH=4 by addition of 10 M NaOH. The reaction mixture was extracted with ethyl acetate, washed with sat. brine, dried over $MgSO_4$, filtered, and evaporated to give (1S,2R)-2-(4-pyridylmethyl)-cyclohexanecarboxylic acid, as a white semi-solid (0.25 g, 90%).

Method P

Synthesis of (4S,5R)-4-benzyl-2-oxo-5-oxazolidinecarboxylic acid

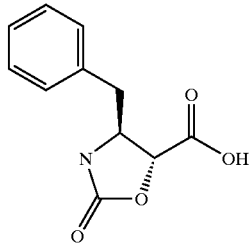

(4S,5R)-4-Benzyl-2-oxo-5-oxazolidinecarboxylic acid was prepared by the method of Herranz, R. et al. *J. Org. Chem.*, 55(7), 2232 (1990).

Example 1

Synthesis of N-[(1S,2R)-2-benzylcyclohex-1-ylcarbonyl]-L-4-(dimethylaminocarbonyloxy)penylalanine,

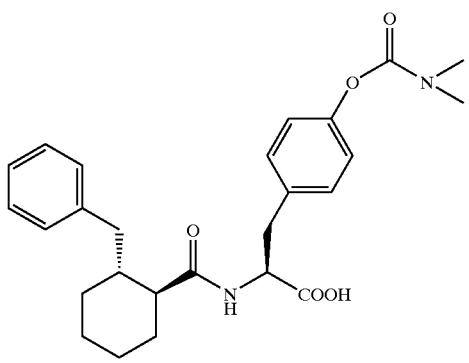

Proceeding as described in Example N above but substituting 1-bromo-3,5-difluorobenzene with bromobenzene gave (1S,2R)-2-benzylcyclohexanecarboxylic acid which was then converted to N-[(1S,2R)-2-benzylcyclohex-1-ylcarbony]1-L-4-(dimethylaminocarbonyloxy)phenylalanine by following the procedures described in Methods I, L, and H above using the appropriate starting materials. NMR data as follows:

$^1$H NMR (CD$_3$)$_2$SO: 8.24 (t, 1H), 7.25–6.89 (m, 9H), 4.53–4.41 (m, 1H), 3.13–3.04 (m, 1H), 3.00 (s, 1.5H), 2.91–2.80 (m, 1H), 2.88 (s, 1.5H), 2.87 (s, 1.5H), 2.83 (s, 1.5H), 2.75 (d, 0.5H), 2.26 (d, 0.5H), 2.08–1.77 (m, 3H), 1.63–0.97 (m, 7H), 0.83–0.66 (m, 1H).

$^{13}$C NMR (CD$_3$)$_2$SO: 175.3, 175.0, 173.6, 154.3, 154.2, 150.1, 150.0, 140.8, 140.7, 134.8, 130.03, 129.99, 129.3, 129.2, 128.2, 128.1, 125.8, 125.6, 121.7, 121.6, 53.2, 53.1, 50.2, 49.8, 36.3, 36.2, 36.1, 36.0, 35.9, 30.0, 25.4, 25.3.

Example 2

Synthesis of N-[(1S,2R)-2-benzylcyclohex-1-ylcarbonyl]-L-4-(thiomorpholin-4-ylcarbonyloxy)phenylalanine

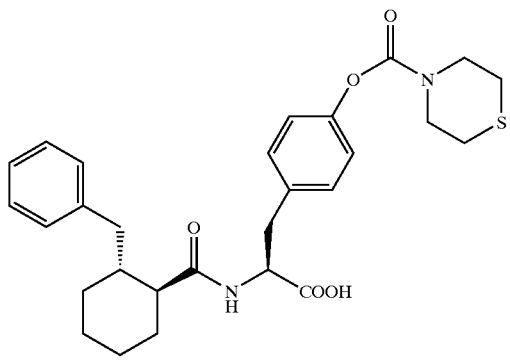

Proceeding as described in Example N above but substituting 1-bromo-3,5-difluorobenzene with bromobenzene gave (1S,2R)-2-benzylcyclohexanecarboxylic acid which was then converted to N-[(1S,2R)-2-benzylcyclohex-1-ylcarbony]1-L-4-(thiomorpholin-4-ylcarbonyloxy)phenylalanine by following the procedures described in Methods I, M (here substituting N-methylpiperazine with thiomorpholine) and H above using the appripate starting materials. NMR data as follows:NMR data was as follows:

$^1$H NMR (CDCl$_3$): 7.27–7.08 (m, 7H), 7:02–6.95 (m, 2H), 6.27 (d, 1H), 5.06–4.93 (m, 1H), 4.24–3.76 (m, 4H), 3.30–3.07 (m, 2H), 2.95–2.57 (m, 5H), 2.18–2.10 (m, 0.5H), 2.04–1.95 (m, 0.5H), 1.90–1.44 (m, 7H), 1.20–1.07 (m, 2H), 0.90–0.74 (m, 1H).

$^{13}$C NMR (CDCl$_3$): 176.4, 176.3, 173.6, 173.5, 153.8, 150.2, 140.3, 133.4, 130.6, 130.4, 129.4, 128.1, 125.8, 121.8, 121.6, 52.6, 52.0, 51.7, 47.0, 46.4, 40.9, 40.6, 40.4, 36.9, 36.4, 30.5, 30.2, 27.3, 27.0, 25.5, 25.3.

Example 3

Synthesis of N-[(1S,2R)-2-benzylcyclohex-1-ylcarbonyl]-L-4-(1,1,-dioxo-thiomorpholin-4-ylcarbonyloxy)phenylalanine

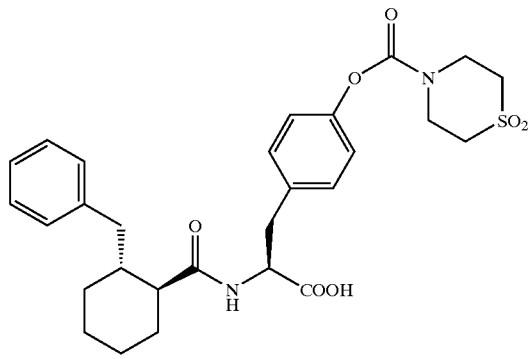

Proceeding as described in Example N above but substituting 1-bromo-3,5-difluorobenzene with bromobenzene gave (1S,2R)-2-benzylcyclohexane-carboxylic acid which was then converted to N-[(1S,2R)-2-benzylcyclohex-1-ylcarbony]1-L-4-(1,1-dioxothiomorpholin-4- ylcarbonyloxy)phenylalanine by following the procedures described in Methods I, M and H above. NMR data as follow:

¹H NMR (CDCl₃): 7.26–6.94 (m, 9H), 6.26–6.20 (m, 1H), 5.06–4.94 (m, 1H), 4.18–3.95 (m, 4H), 3.32–3.24 (m, 0.5H), 3.18–3.00 (m, 5.5H), 2.78 (d, 0.5H), 2.46 (d, 0.5H), 2.18–2.10 (m, 0.5H), 1.98–1.00 (m, 9.5H), 0.92–0.72 (m, 1H).

¹³C NMR (CDCl₃): 176.5, 174.0, 173.9, 153.4, 153.3, 149.8, 140.3, 140.2, 133.9, 130.6, 130.5, 129.4, 128.1, 128.1, 125.9, 125.8, 121.6, 64.0, 63.9, 52.5, 52.0, 51.6, 43.0, 40.9, 40.6, 40.4, 36.9, 36.5, 30.5, 30.2, 27.3, 27.0, 25.5, 25.3.

Example 4

Synthesis of N-[(1S,2R)-2-(3,5-difluorobenzyl) cyclohex-1-ylcarbonyl]-L-4- (dimethylaminocarbonyloxy)phenylalanine

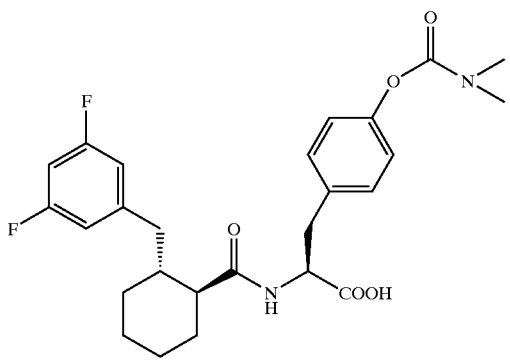

The product formed in Method N above was converted to N-[(1S,2R)-2-(3,5-difluorobenzyl)cyclohex-1-ylcarbonyl]-L-4-(dimethylaminocarbonyl-oxy)phenylalanine by following the methods described in I, L and H above using the appropriate starting materials. NMR data as follows:

¹H NMR (CD₃OD): 8.39–8.35 (m, 1H), 7.26 (d, 3H), 6.99 (d, 1H), 6.91 (d, 1H), 6.74–6.67 (m, 3H), 6.60 (d, 1H), 4.85–4.80 (m, 1H), 4.73–4.70 (m, 1H), 3.50–3.22 (m, 2H), 3.22–2.82 (m, 10H), 2.18–1.07 (m, 14H), 0.9–0.7 (m, 2H).

¹³C NMR (CD₃OD): 178.8, 178.8, 178.5, 178.4, 174.9, 166.1, 165.9, 162.8, 162.7, 156.9, 156.7, 151.8, 151.7, 146.9, 146.8, 146.7, 136.0, 135.9, 131.3, 131.2, 122.9, 122.9, 113.3, 113.2, 113.1, 112.9, 102.3, 102.2, 101.9, 101.8, 101.6, 101.5, 54.7, 54.6, 54.4, 54.3, 52.5, 52.1, 52.0, 41.7, 41.4, 37.8, 37.4, 36.8, 36.7, 36.6, 36.5, 31.5, 31.4, 31.3, 26.6.

Example 5

Synthesis of N-(trans-2-(3,4-difluorobenzyl) cyclohex-1-ylcarbonyl)-L-4- (dimethylaminocarbonyloxy)phenylalanine

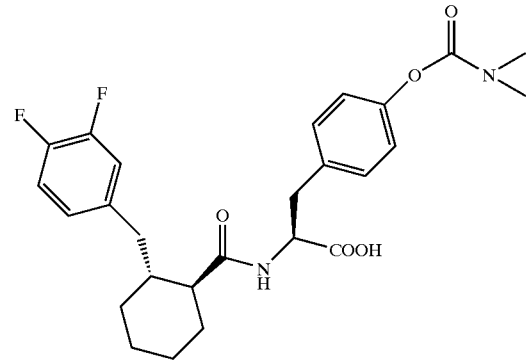

Proceeding as described in Example N above but substituting 1-bromo-3,5-difluorobenzene with 1-bromo-3,4-difluorobenzene gave (1S,2R)-2-(3,4-difluorobenzyl) cyclohexane-carboxylic acid which was then converted to N-[(1S,2R)-2-(3,4-difluorobenzyl)cyclohex-1-ylcarbonyl]-L-4-(dimethylaminocarbonyloxy)phenylalanine by following the procedures described in Methods I, L and H above, using the appropriate starting materials. NMR data as follows:

¹H NMR (CD₃OD): 8.38–8.33 (m, 1H), 7.26 (d, 2H), 7.14–6.8 (m, 6H), 6.77–6.74 (m, 1H), 4.86–4.78 (m, 1H), 4.75–4.67 (m, 1H), 3.20–2.73 (m, 9H), 2.16–1.07 (m, 14H), 0.87–0.76 (m, 2H).

¹³C NMR (CD₃OD): 172.9, 172.4, 168.9, 150.6, 145.8, 145.7, 137.3, 133.6, 130.0, 129.9, 125.3, 125.2, 120.5, 116.9, 116.8, 113.0, 112.9, 112.8, 111.7, 111.5, 48.6, 48.5, 46.5, 46.0, 35.8, 34.9, 31.8, 31.5, 30.8, 30.7, 30.6, 30.4, 25.6, 25.5, 25.4, 25.3, 20.7.

Example 6

Synthesis of N-[(1S,2R)-2-(pyridin-3-ylmethyl) cyclohex-1-ylcarbonyl]-L-4- (dimethylaminocarbonyloxy)phenylalanine

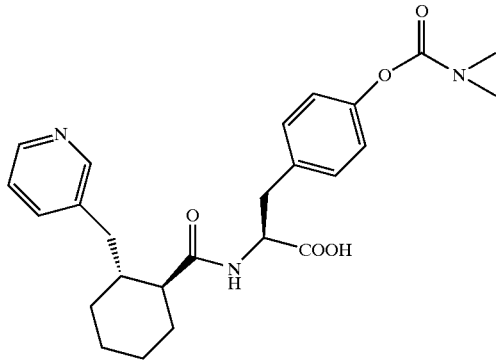

Proceeding as described in Example O above but substituting 4-bromopyridine with 3-bromopyridine gave (1S, 2R)-2-(pyridin-3-ylmethyl)cyclohexanecarboxylic acid which was then converted to N-[(1S,2R)-2-(pyridin-3-ylmethyl)cyclohex-1-ylcarbony]1-L-4-

(dimethylaminocarbonyloxy)phenylalanine by following the procedures described in Methods I, L and H above, using the appropriate starting materials. NMR data was as follows:

$^{1}$H NMR (CD$_3$OD): 8.30–8.15 (m, 3H), 7.63 (d, 1H), 7.47 (d, 1H), 7.35–7.23 (m, 4H), 6.97 (d, 2H), 6.83 (d, 2H), 4.73–4.68 (m, 1H), 4.55–4.51 (m, 1H), 3.34–3.21 (m, 2H), 3.08 (s, 3H), 3.03–2.75 (m, 11H), 2.24–2.16 (m, 1H), 2.04–0.78 (m, 18H).

$^{13}$C NMR (CD$_3$OD): 179.9, 176.7, 172.9, 172.4, 171.6, 171.4, 168.8, 150.6, 145.5, 145.4, 144.8, 141.5, 141.4, 133.3, 133.2, 131.3, 131.0, 125.5, 125.4, 122.6, 119.1, 116.5, 51.1, 50.9, 46.9, 46.6, 35.8, 35.6, 33.3, 32.8, 32.5, 30.7, 30.6, 25.8, 25.4, 25.3, 25.2, 20.6.

Example 7

Synthesis of N-[(1S,2R)-2-(pyridin-4-ylmethyl)cyclohex-1-ylcarbonyl]-L-4-(dimethylaminocarbonyloxy)phenylalanine

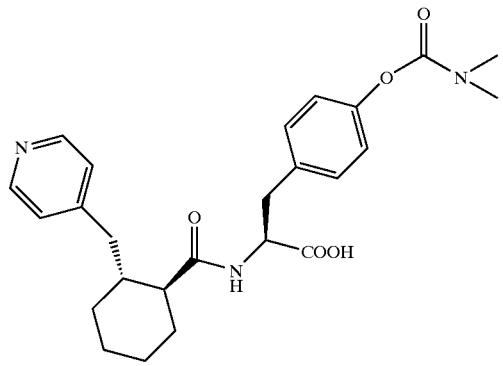

The product formed in Method O above was converted to N-[(1S,2R)-2-(pyridin-4-ylmethyl)cyclohex-1-ylcarbonyl]-L-4-(dimethylaminocarbonyloxy)phenylalanine by following the methods described in I, L and H above using the appropriate starting materials. NMR data as follows: NMR data was as follows:

$^{1}$H NMR (CD$_3$OD): 8.37–8.33 (m, 4H), 7.28–7.20 (m, 6H), 7.06 (d, 2H), 6.96 (d, 2H), 6.83 (d, 2H), 4.72–4.68 (m, 1H), 4.55–4.52 (m, 1H), 3.08–2.76 (m, 15H), 2.26–2.22 (m, 1H), 2.05–0.83 (m, 26H).

$^{13}$C NMR (CD$_3$OD): 172.9, 172.4, 171.4, 171.3, 150.9, 150.6, 147.1, 147.0, 145.5, 145.3, 143.6, 131.2, 131.0, 125.5, 125.4, 120.7, 120.6, 116.5, 51.1, 50.9, 46.9, 46.57 35.3, 35.3, 35.2, 35.1, 33.4, 32.5, 30.7, 30.6, 30.5, 25.8, 25.6, 25.4, 25.1, 20.6.

Example 8

Synthesis of N-[(4S,5R)-4-benzyl-2-oxo-oxazolidin-5-ylcarbonyl]-L-4-(dimethylaminocarbonyloxy)phenylalanine

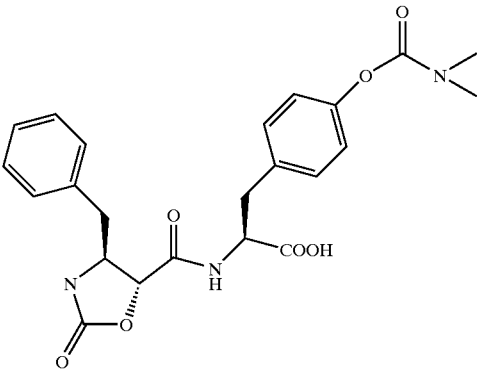

The product formed in Method P above was converted to N-[(4S,5R)-4-benzyl-2-oxo-oxazolidin-5-ylcarbonyl]-L-4-(dimethylaminocarbonyloxy)phenylalanine by following the methods described in I, L and H above using the appropriate starting materials. NMR data was as follows:

$^{1}$H NMR (CD$_3$OD): 8.39 (d, 1H), 7.46 (m, 7H), 7.11 (m, 2H), 4.85 (m, 1H), 4.70 (m, 1H), 3.99 (m, 1H), 3.39 (m, 1H), 3.21–2.88 (m, 10H).

$^{13}$C NMR (CD$_3$OD): 174.1, 17.1.3, 156.9, 152.0, 160.1, 137.3, 135.7, 131.4, 130.9, 129.9, 128.2, 123.1, 79.0, 58.6, 54.6, 42.1, 37.3, 36.9, 36.7.

Example 9

Synthesis of N-((4S,5R)-4-benzyl-2-oxo-oxazolidin-5-ylcarbonyl)-L-phenylalanine

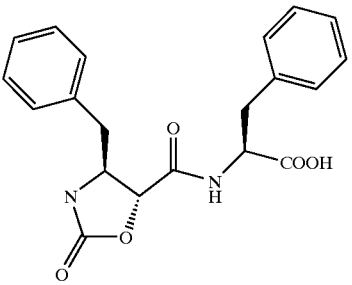

The product formed in Method P above was converted to N-[(4S,5R)-4-benzyl-2-oxo-oxazolidin-5-ylcarbonyl]-L-4-phenylalanine by following the methods described in I and H above using the appropriate starting materials. NMR data was as follows:

$^{1}$H NMR (CDCl$_3$): 7.37–7.09 (m, 10H), 6.52 (s, 1H), 4.84 (m, 1H), 4.45 (d, 1H), 4.09 (m, 1H), 3.18 (m, 1H), 3.00 (m, 2H), 2.72 (m, 1H).

$^{13}$C NMR (CDCl$_3$): 173.5, 168.9, 158.3, 135.9, 135.1, 129.5, 129.2, 128.9, 128.6, 127.3, 127.1, 77.7, 57.1, 53.1, 41.2, 36.9.

Formulation Examples

The following formulation-examples illustrate the pharmaceutical compositions of the present invention.

Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Example 9

An intravenous formulation may be prepared as follows:

| Ingredient | Quantity |
| --- | --- |
| Active Ingredient | 250.0 mg |
| Isotonic saline | 1000 ml |

Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Biological Examples

Example 1

Cell Adhesion Assay

Compounds of this invention may be tested for their ability to inhibit cellular adhesion. Using RPMI-8866 cells, adhesion to recombinant, immobilized soluble MadCAM-1 is measured. This assay is described by Tidswell et al., *J. Immunol.* (1997) 159(3):1497–1505.

Example 2

Soluble MadCAM-1 FACS Assay

This assay measures the interaction of recombinant soluble MadCAM-1 with RPMI-8866 cells in suspension. Recombinant soluble MadCAM-1 ("rsMadCAM-1") is expressed as a fusion protein with a human IgG Fc tail (Tidswell et al., *J. Immunol.* (1997) 159(3):1497–1505). Soluble MadCAM-1 is mixed with RPMI-8866 cells in the presence and absence of small molecule inhibitors. 1 mM MnCl$_2$ is included in the assay buffer to increase the activity of $\alpha_4\beta_7$ integrin and to promote its interaction with the MadCAM-1 construct. After 30 minutes at room temperature, the cells are washed with buffer containing 1 mM MnCl$_2$ and are exposed to fluorescent-labeled antibody against the Fc tail of the MadCAM-1 fusion protein in the presence of 1 mM MnCl$_2$ for 30 minutes at 4° C. The cells are washed, resuspended in MnCl$_2$ containing buffer and examined by FACS analysis. An identical assay can be performed to measure the interaction of recombinant soluble VCAM-1 with cells that express $\alpha_4\beta_1$, such as the Jurkat T cell line.

Example 3

Cell Free ELISA Assay

This assay measures the interaction of solubilized $\alpha_4\beta_7$ integrin with MadCAM-1 which has been immobilized on plastic. RPMI-8866 cells are lysed with a detergent to solubilize $\alpha_4\beta_7$ integrin. Antibody against β7 integrin, 2G3 (Tidswell et al. *J. Immunol.* (1997) 159(3):1497–1505), is added to the lysate. This antibody serves two purposes, first, it is a tag by which $\alpha_4\beta_7$ integrin can be detected in the assay and, second, 2G3 is an antibody that stabilizes a ligand occupied conformation of $\beta_7$ intern and promotes $\beta_7$ integrin-dependent interactions. Cell lysante, 2G3, and test compound are added to microtiter wells that have been coated with MadCAM-1. The mixture is allowed to incubate for 30 minutes at room temperature. The plate is washed, blocked with 1% BSA, and exposed to HRP-conjugated goat anti-mouse Ig, which recognizes 2G3 associated with $\alpha_4\beta_7$ integrin that has bound MadCAM-1 on the assay well. After 30 minutes at room temperature, the wells are washed and exposed to a substrate for HRP to quantify the amount of $\alpha_4\beta_7$ integrin that has bound MadCAM-1.

Example 4

FACS Assay for Receptor Occupancy

This assay measures the interaction of antibody 2G3 with RPMI-8866 cells or with lymphocytes. The antibody recognizes a ligand-occupied epitope of either rat or human $\beta_7$ integrin. Increasing concentrations of small molecule ligand induce the 2G3 epitope on $\beta_7$ integrin and will allow higher levels of antibody binding to the surface of the cells. The concentration of ligand required for receptor occupancy is directly related to the ligand's affinity for $\alpha_4\beta_7$ integrin. A similar assay has been described for examining the interaction of ligands withe $\alpha_4\beta_1$ integrin, which utilizes an analogous antibody against a ligand occupied epitope of $\beta_1$ integrin (antibody 15/7; Yednock et al. (1995) *JBC* 270:28740–50). The $\beta_1$ integrin assay relies on cells that express $\alpha_4\beta_1$ integrin, rather than $\alpha_4\beta_7$ integrin (such as Jurkat celles). In both assays, the appropriate celles are mixed with either 2G3 or 15/7 in the presence of the small molecule ligand. The cells are incubated at room temperature for 30 minutes and washed to remove unbound antibody. The cells are exposed to a fluorescently-labeled antibody agianst mouse IgG, which detects cell-associated 2G3 or 15/7 and the cellare are examined by FACS analysis.

Example 5

Ex vivo Cell Adhesion Assay

This assay measures the adhesion of lymphocytes or RPMI-8866 cells to high endothelial venules exposed in tissue sections of Peyer's Patches (lymphoid tissue associated with the intestine). These vessels express high levels of MadCAM-1. This assay is described by Yednock et al., *JCB* (1987) 104:725–731.

Example 6

In vivo Migration Assay

Migration of In[111]-labeled or fluorescently-labeled lymphocytes to Peyer's Patches in vivo. In this assay, lymphocytes are isolated from one group of animals and are labeled with a radioactive or fluorescent tracer. The cells are injected intravenously into a second group of animals. After 1 to 24 hours, the localization of the labeled cells to different tissues can be monitored by either determining the number of radioactive counts associated with different tissues in a gamma counter, or by isolating lymphocytes from the tissue and determining the number of cells that carry a fluorescent tag (determined by FACS analysis). This type of assay is described by Rosen et al., *J. Immunol.* (1989) 142:1895–1902. Compounds of this invention were tested using this assay and were shown to inhibit migration of cells.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I:

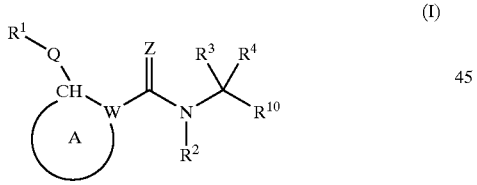

(I)

wherein:

A together with —CH— and W forms a heterocyclic or substituted heterocyclic group;

Q is selected from the group consisting of alkylene, substituted alkylene, —CO—, —NR$^5$— (where R$^5$ is hydrogen, alkyl, or acyl), —O—, or —S(O)$_q$ where q is an integer from 0 to 2;

W is —CH— or —N—;

Z is —O— or —S—;

R$^1$ is selected from the group consisting of aryl, substituted aryl, heteroaryl, substituted heteroaryl, heterocyclic, substituted heterocyclic, cycloalkyl, and substituted cycloalkyl;

R$^2$ is selected from the group consisting of hydrogen, alkyl which is optionally substituted with one to four substituents independently selected from R$^a$ and Cy which is optionally substituted with one to four substituents independently selected from R$^b$ wherein R$^a$ and R$^b$ are as defined below;

R$^3$ is selected from the group consisting of:
(a) -(alkylene)-Ar—R$^6$, -(alkenylene)-Ar—R$^6$, or -(alkynylene)-Ar—R$^6$ where:
Ar is selected from the group consisting of aryl, heteroaryl, or heterocyclic wherein said aryl, heteroaryl, and heterocyclic rings are optionally substituted with one or two substituents independently selected from R$^a$ wherein R$^a$ is as defined below;
R$^6$ is selected from the group consisting of —O—Y—NR$^7$R$^8$ and —O—Y—R$^9$ wherein Y is selected from the group consisting of —C(O)— and —SO$_2$—; R$^7$ and R$^8$ are independently selected from the group consisting of hydrogen, alkyl, substituted alkyl, cycloalkyl, heterocyclic, and substituted heterocyclic; or R$^7$ and R$^8$ are joined to form a heterocycle or substituted heterocycle; and R$^9$ is heterocycle or substituted heterocycle;
(b) -(alkyene)-Ar$^2$—Ar$^1$,-(alkenylene)-Ar$^2$-Ar$^1$ and -(alkynylene)-Ar$^2$—Ar$^1$, wherein Ar$^1$ and Ar$^2$ are independently aryl or heteroaryl each of which is optionally substituted with one to four substituents independently selected from R$^b$ as defined below; and alkylene, alkenylene and alkynylene are optionally substituted with one to four substituents independently selected from R$^a$ as defined below;

R$^4$ is selected from the group consisting of hydrogen, alkyl, alkenyl, alkynyl, aryl, aryl-C$_{1-10}$alkyl, heteroaryl, and heteroaryl-C$_{1-10}$ alkyl wherein alkyl, alkenyl and alkynyl are optionally substituted with one to four substituents selected from R$^a$ as defined below; and aryl and heteroaryl are optionally substituted with one to four substituents independently selected from R$^b$ as defined below;

R$^a$ is selected from the group consisting of Cy, —OR$^d$, —NO$_2$, halogen, —S(O)$_m$R$^d$, —SR$^d$, —S(O)$_2$OR$^d$, —S(O)$_m$NR$^d$R$^e$, —NR$^d$R$^e$, —O(CR$^f$R$^g$)$_n$NR$^d$R$^e$, —C(O)R$^d$, —CO$_2$R$^d$, —CO$_2$(CR$^f$R$^g$)$_n$CONR$^d$R$^e$, —OC(O)R$^d$, —CN, —C(O)NR$^d$R$^e$, —NR$^d$C(O)R$^e$, —OC(O)NR$^d$R$^e$, —NR$^d$C(O)OR$^e$, —NR$^d$C(O)NR$^d$R$^e$, —CR$^d$(N—OR$^e$), CF$_3$, and —OCF$_3$; wherein Cy is optionally substituted with one to four substituents independently selected from R$^c$ wherein:
R$^c$ is selected from the group consisting of halogen, amino, carboxy, C$_{1-4}$ alkyl, C$_{1-4}$ alkoxy, aryl, aryl-C$_{1-4}$ alkyl, hydroxy, CF$_3$, and aryloxy;
R$^d$ and R$^e$ are independently selected from hydrogen, alkyl, alkenyl, alkynyl, Cy and Cy-alkyl wherein alkyl, alkenyl, alkynyl and Cy are optionally substituted with one to four substituents independently selected from R$^c$; or R$^d$ and R$^e$ together with the atoms to which they are attached form a heterocyclic ring of 5 to 7 atoms and containing 0–2 additional heteroatoms independently selected from oxygen, sulfur and nitrogen; and
R$^f$ and R$^g$ are independently selected from hydrogen, alkyl, Cy and Cy-alkyl; or R$^f$ and R$^g$ together with the carbon to which they are attached form a ring of 5 to 7 atoms containing 0–2 heteroatoms independently selected from oxygen, sulfur and nitrogen;

R$^b$ is selected from the group consisting of R$^a$ as defined above, alkyl, alkenyl, alkynyl, aryl-C$_{1-10}$ alkyl, heteroaryl-C$_{1-10}$ alkyl, wherein alkyl, alkenyl, alkynyl, aryl, heteroaryl are optionally substituted with a group independently selected from $R^c$;

Cy is cycloalkyl, heterocyclyl, aryl, or heteroaryl; and $R^{10}$ is selected from the group consisting of —C(O)OR$^d$, —P(O)(OR$^d$)(OR$^e$), —P(O)(R$^d$)(OR$^e$), —S(O)$_m$OR$^d$, —C(O)NR$^d$R$^h$, and -5-tetrazolyl where:

$R^d$ and $R^e$ are as defined above;

$R^h$ is selected from the group consisting of hydrogen, alkyl, alkenyl, alkynyl, cyano, aryl, aryl-C$_{1-10}$ alkyl, heteroaryl, heteroaryl-C$_{1-10}$ alkyl, or —SO$_2$R$^i$ wherein alkyl, alkenyl, and alkynyl are optionally substituted with one to four substitutents independently selected from R$^a$; and aryl and heteroaryl are each optionally substituted with one to four substituents independently selected from R$^b$ where R$^a$ and R$^b$ are as defined above;

$R^i$ is selected from the group consisting of alkyl, alkenyl, alkynyl, and aryl wherein alkyl, alkenyl, alkynyl and aryl are each optionally substituted with one to four substituents independently selected from R$^c$;

m is an integer from 1 to 2; and n is an integer from 1 to 10; or pharmaceutically acceptable salts, individual isomer, mixtures of isomers, and prodrugs thereof.

2. The compound of claim 1 where:

$R^1$ is aryl or substituted aryl;

$R^2$ and $R^4$ are hydrogen; and $R^{10}$ is —COOR$^d$ where R$^d$ is hydrogen or alkyl.

3. The compound of claim 2 where Q is alkylene; Z is —O—; and R$^3$ is -(alkylene)-Ar—R$^6$ where Ar is aryl optionally substituted with one or two substituents independently selected from R$^a$; and R$^6$ is —O—C(O)NR$^7$R$^8$ where R$^7$ and R$^8$ are independently selected from the group consisting of hydrogen, alkyl, substituted alkyl, cycloalkyl, heterocyclic, or substituted heterocyclic; or R$^7$ and R$^8$ are joined to form a heterocycle or substituted heterocycle.

4. The compound of claim 3 wherein Q is —CH$_2$—; and R$^3$ is —(CH$_2$)—Ar—R$^6$ where Ar is aryl optionally substituted with one or two substituents independently selected from R$^a$; and R$^6$ is —O—C(O)NR$^7$R$^8$ where R$^7$ and R$^8$ are independently selected from the group consisting of hydrogen, alkyl, substituted alkyl, cycloalkyl, heterocyclic, or substituted heterocyclic; or R$^7$ and R$^8$ are joined to form a heterocycle or substituted heterocycle.

5. The compound of claim 1 where R$^1$ is aryl or substituted aryl.

6. The compound of claim 5 where Z is —O—; R$^2$ and R$^4$ are hydrogen; and R$^{10}$ is —COOR$^d$ where R$^d$ is hydrogen or alkyl.

7. The compound of claim 1 where R$^1$ is heteroaryl or substituted heteroaryl.

8. The compound of claim 7 where Z is —O—; R$^2$ and R$^4$ are hydrogen; and R$^{10}$ is —COOR$^d$ where R$^d$ is hydrogen or alkyl.

9. The compound of claim 1 where R$^3$ is -(alkylene)-Ar—R$^6$ where Ar is aryl optionally substituted with one or two substituents independently selected from R$^a$; and R$^6$ is —O—C(O)NR$^7$R$^8$ where R$^7$ and R$^8$ are independently selected from the group consisting of hydrogen, alkyl, substituted alkyl, cycloalkyl, heterocyclic, or substituted heterocyclic; or R$^7$ and R$^8$ are joined to form a heterocycle or substituted heterocycle.

10. The compound of claim 9 wherein R$^3$ is —(CH$_2$)—Ar—R$^6$ where Ar is aryl optionally substituted with one or two substituents independently selected from R$^a$; and R$^6$ is —O—C(O)NR$^7$R$^8$ where R$^7$ and R$^8$ are independently selected from the group consisting of hydrogen, alkyl, substituted alkyl, cycloalkyl, heterocyclic, or substituted heterocyclic; or R$^7$ and R$^8$ are joined to form a heterocycle or substituted heterocycle.

11. The compound of claim 10 wherein Z is —O—; R$^2$ and R$^4$ are hydrogen; R$^{10}$ is —COOR$^d$ where R$^d$ is hydrogen or alkyl; and R$^3$ is —(CH$_2$)—Ar—R$^6$ where Ar is phenyl and R$^6$ is —O—C(O)NR$^7$R$^8$ where R$^7$ and R$^8$ are independently selected from the group consisting of hydrogen or alkyl.

12. The compound of claim 11 where Z is —O—; R$^2$ and R$^4$ are hydrogen; and R$^{10}$ is —COOR$^d$ where R$^d$ is hydrogen or alkyl.

13. The compound of claim 12 where R$^3$ is -(alkylene)-Ar—R$^6$ where Ar is aryl optionally substituted with one or two substituents independently selected from R$^a$; and R$^6$ is —O—C(O)NR$^7$R$^8$ where R$^7$ and R$^8$ are independently selected from the group consisting of hydrogen, alkyl, substituted alkyl, cycloalkyl, heterocyclic, or substituted heterocyclic; or R$^7$ and R$^8$ are joined to form a heterocycle or substituted heterocycle.

14. A method for binding $\alpha_4\beta_7$ receptor in a biological sample which method comprises contacting the biological sample with a compound of claim under conditions wherein said compound binds to $\alpha_4\beta_7$ receptor.

15. A pharmaceutical composition comprising a pharmaceutically acceptable carrier and a therapeutically effective amount of one or more of a compound of claim 1.

16. A method of treatment of a disease in a mammal treatable by administration of a $\alpha_4\beta_7$ receptor antagonist, comprising administration to the mammal of a therapeutically effective amount of a compound of claim 1.

17. A method of treatment of a disease in a mammal treatable by administration of a $\alpha_4\beta_7$ receptor antagonist, comprising administration to the mammal of a therapeutically effective amount of a pharmaceutical compositions of claim 15.

18. The method of claim 17 wherein the disease is an inflammatory disease.

19. A compound of Formula IA:

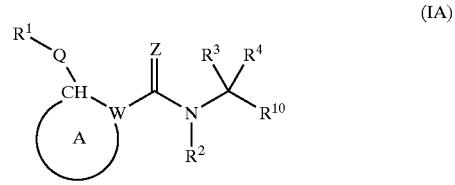

(IA)

wherein:

A together with —CH— and W forms an unfused cyclic group selected from the group consisting of heterocyclic, and substituted heterocyclic;

Q is selected from the group consisting of alkylene, substituted alkylene, —CO—, —NR$^5$— (where R$^5$ is hydrogen, alkyl, or acyl), —O—, or —S(O)$_q$ where q is an integer from 0 to 2;

W is —CH—;

Z is —O—or —S—;

R$^1$ is selected from the group consisting of aryl, substituted aryl, cycloalkyl, and substituted cycloalkyl;

R$^2$ is selected from the group consisting of hydrogen, alkyl which is optionally substituted with one to four substituents independently selected from R$^1$, and Cy which is optionally substituted with one to four substituents independently selected from $R^b$, wherein $R^a$ and $R^b$ are as defined below;

$R^3$ is selected from the group consisting of:
(a) -(alkylene)-Ar—$R^6$, -(alkenylene)-Ar—$R^6$, or -(alkynylene)-Ar—$R^6$ where:
   Ar is selected from the group consisting of aryl or optionally substituted aryl with one or two substituents independently selected from $R^a$, wherein $R^a$ is as defined below;
   $R^6$ is selected from the group consisting of—O—Y—$NR^7R^8$ wherein Y is selected from the group consisting of—C(O)— and —$SO_2$—; $R^7$ and $R^8$ are independently selected from the group consisting of hydrogen, alkyl, substituted alkyl, cycloalkyl;
(b) -(alkyene)-$Ar^2$—$Ar^1$,-(alkenylene)-$Ar^2$—$Ar^1$ and -(alkynylene)-$Ar^2$—$Ar^1$, wherein $Ar^1$ and $Ar^2$ are independently aryl each of which is optionally substituted with one to four substituents independently selected from $R^b$ as defined below; and alkylene, alkenylene and alkynylene are optionally substituted with one to four substituents independently selected from $R^a$ as defined below;

$R^4$ is selected from the group consisting of hydrogen, alkyl, alkenyl, alkynyl, aryl, aryl-$C_{1-10}$ alkyl, wherein alkyl, alkenyl and alkynyl are optionally substituted with one to four substituents selected from $R^a$ as defined below; and aryl is optionally substituted with one to four substituents independently selected from $R^b$ as defined below;

$R^a$ is selected from the group consisting of Cy, —$OR^d$, —$NO_2$, halogen—$S(O)_m R^d$, —$SR^d$, —$S(O)_2 OR^d$, —$S(O)_m NR^d R^e$, —$NR^d R^e$, —$O(CR^f R^g)_n NR^d R^e$, —$C(O)R^d$, —$CO_2 R^d$, —$CO_2(CR^f R^g)_n CONR^d R^e$, —$OC(O)R^d$, —CN, —$C(O)NR^d R^e$, —$NR^d C(O)R^e$, —$OC(O)NR^d R^e$, —$NR^d C(O)OR^e$, —$NR^d C(O)NR^d R^e$, —$CR^d(N—OR^e)$, $CF_3$, and —$OCF_3$; wherein Cy is optionally substituted with one to four substituents independently selected from $R^c$ wherein:
   $R^c$ is selected from the group consisting of halogen, amino, carboxy, $C_{1-4}$ alkyl, $C_{1-4}$ alkoxy, aryl, aryl-$C_{1-4}$ alkyl, hydroxy, $CF_3$, and aryloxy;
   $R^d$ and $R^e$ are independently selected from hydrogen, alkyl, alkenyl, alkynyl, Cy and Cy-alkyl wherein alkyl, alkenyl, alkynyl and Cy are optionally substituted with one to four substituents independently selected from $R^c$;
   $R^f$ and $R^g$ are independently selected from hydrogen, alkyl, Cy and Cy-alkyl;

$R^b$ is selected from the group consisting of $R^a$ as defined above, alkyl, alkenyl, alkynyl, aryl-$C_{1-10}$ alkyl, wherein alkyl, alkenyl, alkynyl, aryl, are optionally substituted with a group independently selected from $R^c$;

Cy is cycloalkyl, or aryl; and $R^{10}$ is selected from the group consisting of —$C(O)OR^d$, —$P(O)(OR^d)(OR^e)$, —$P(O)(R^d)(OR^e)$, —$S(O)_m OR^d$, —$C(O)NR^d R^h$, and where:
   $R^d$ and $R^e$ are as defined above;
   $R^h$ is selected from the group consisting of hydrogen, alkyl, alkenyl, alkynyl, cyano, aryl, aryl-$C_{1-10}$ alkyl, or —$SO_2 R^i$ wherein alkyl, alkenyl, and alkynyl are optionally substituted with one to four substitutents independently selected from $R^a$; and aryl is optionally substituted with one to four substituents independently selected from $R^b$ where $R^a$ and $R^b$ are as defined above;

$R^i$ is selected from the group consisting of alkyl, alkenyl, alkynyl, and aryl wherein alkyl, alkenyl, alkynyl and aryl are each optionally substituted with one to four substituents independently selected from $R^c$;

m is an integer from 1 to 2; and n is an integer from 1 to 10;

or pharmaceutically acceptable salts, individual isomer, mixtures of isomers, and prodrugs thereof.

20. The compound of claim 19 wherein:

$R^1$ is aryl or substituted aryl;

$R^2$ and $R^4$ are hydrogen; and $R^{10}$ is —$COOR^d$ where $R^d$ is hydrogen or alkyl.

21. The compound of claim 20 where Q is alkylene; Z is —O—; and $R^3$ is -(alkylene)-Ar—$R^6$ where Ar is aryl optionally substituted with one or two substituents independently selected from $R^a$; and $R^6$ is —O—$C(O)NR^7 R^8$ where $R^7$ and $R^8$ are independently selected from the group consisting of hydrogen, alkyl, substituted alkyl, or cycloalkyl.

22. The compound of claim 21 wherein Q is —$CH_2$—; and $R^3$ is —$(CH_2)$—Ar—$R^6$ where Ar is aryl optionally substituted with one or two substituents independently selected from $R^a$; and $R^6$ is —O—$C(O)NR^7 R^8$ where $R^7$ and $R^8$ are independently selected from the group consisting of hydrogen, alkyl, substituted alkyl, or cycloalkyl.

23. The compound of claim 19 where $R^1$ is aryl or substituted aryl.

24. The compound of claim 23 where Z is —O—; $R^2$ and $R^4$ are hydrogen; and $R^{10}$ is —$COOR^d$ where $R^d$ is hydrogen or alkyl.

25. The compound of claim 19 where $R^3$ is -(alkylene)-Ar—$R^6$ where Ar is aryl optionally substituted with one or two substituents independently selected from $R^a$; and $R^6$ is —O—$C(O)NR^7 R^8$ where $R^7$ and $R^8$ are independently selected from the group consisting of hydrogen, alkyl, substituted alkyl, or cycloalkyl.

26. The compound of claim 25 wherein $R^3$ is —$(CH_2)$—Ar—$R^6$ where Ar is aryl optionally substituted with one or two substituents independently selected from $R^a$; and $R^6$ is —O—$C(O)NR^7 R^8$ where $R^7$ and $R^8$ are independently selected from the group consisting of hydrogen, alkyl, substituted alkyl, or cycloalkyl.

27. The compound of claim 26 wherein Z is —O—; $R^2$ and $R^4$ are hydrogen; $R^{10}$ is —$COOR^d$ where $R^d$ is hydrogen or alkyl; and $R^3$ is —$(CH_2)$—Ar—$R^6$ where Ar is phenyl and $R^6$ is —O—$C(O)NR^7 R^8$ where $R^7$ and $R^8$ are independently selected from the group consisting of hydrogen or alkyl.

28. A pharmaceutical composition comprising a pharmaceutically acceptable carrier and a therapeutically effective amount of one or more of a compound of claim 19.

29. A method for binding $\alpha_4 \beta_7$ receptor in a biological sample which method comprises contacting the biological sample with a compound of claim 19 under conditions wherein said compound binds to $\alpha_4 \beta_7$ receptor.

30. A method of treatment of a disease in a mammal treatable by administration of a $\alpha_4 \beta_7$ receptor antagonist, comprising administration to the mammal of a therapeutically effective amount of a compound of claim 19.

31. A method of treatment of a disease in a mammal treatable by administration of a $\alpha_4 \beta_7$ receptor antagonist, comprising administration to the mammal of a therapeutically effective amount of a pharmaceutical compositions of claim 28.

32. The method of claim 31 wherein the disease is an inflammatory disease.

33. A compound of the formula
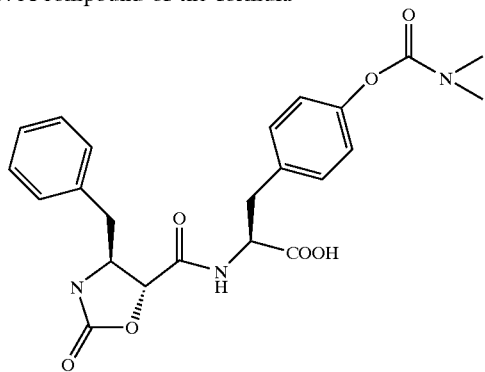
and pharmaceutically acceptable salts thereof.
34. A compound of the formula
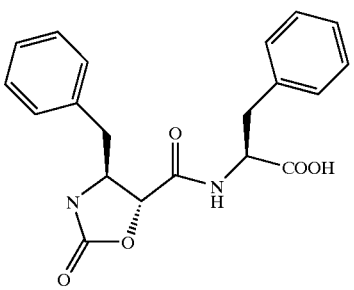
and pharmaceutically acceptable salts thereof.
* * * * *